US009644187B2

(12) United States Patent
Asher et al.

(10) Patent No.: US 9,644,187 B2
(45) Date of Patent: May 9, 2017

(54) METHODS OF PRODUCING HIGH TITER, HIGH PURITY VIRUS STOCKS AND METHODS OF USE THEREOF

(75) Inventors: Damon R. Asher, Jefferson, MA (US); Amanda B. Katz, Windham, NH (US); Navid Z. Khan, Tewksbury, MA (US); Ushma Mehta, N. Chelmsford, MA (US)

(73) Assignee: EMD Millipore Corporation, Billerica, MA (US)

( * ) Notice: Subject to any disclaimer, the term of this patent is extended or adjusted under 35 U.S.C. 154(b) by 0 days.

(21) Appl. No.: 13/082,828

(22) Filed: Apr. 8, 2011

(65) Prior Publication Data

US 2012/0088228 A1    Apr. 12, 2012

Related U.S. Application Data

(60) Provisional application No. 61/324,220, filed on Apr. 14, 2010.

(51) Int. Cl.
| | | |
|---|---|---|
| *C12N 7/00* | (2006.01) | |
| *C12N 7/02* | (2006.01) | |
| *C12Q 1/70* | (2006.01) | |
| *G01N 33/569* | (2006.01) | |

(52) U.S. Cl.
CPC ...... *C12N 7/00* (2013.01); *C12N 2750/14351* (2013.01)

(58) Field of Classification Search
CPC .......... C12N 7/025; C12N 2750/14151; C12N 15/1017; C12N 15/101
USPC .......................................................... 435/5
See application file for complete search history.

(56) References Cited

U.S. PATENT DOCUMENTS

| | | |
|---|---|---|
| 3,622,663 A | 11/1971 | Lapidus |
| 3,919,044 A | 11/1975 | Melnick et al. |
| 4,071,619 A | 1/1978 | Peradze et al. |
| 4,522,809 A | 6/1985 | Adamowicz et al. |
| 4,724,210 A | 2/1988 | Oka et al. |
| 4,725,546 A | 2/1988 | Sakamoto et al. |
| 4,725,547 A | 2/1988 | Sakamoto et al. |
| 4,814,268 A | 3/1989 | Kreider et al. |
| 5,268,292 A | 12/1993 | Robertson et al. |
| 5,521,082 A | 5/1996 | Lewis et al. |
| 5,597,721 A | 1/1997 | Brun et al. |
| 5,602,023 A | 2/1997 | Csatary |
| 5,607,851 A | 3/1997 | Pellegrini et al. |
| 5,624,795 A | 4/1997 | Piot et al. |
| 5,645,984 A | 7/1997 | Nader |
| 5,658,779 A | 8/1997 | Krupey et al. |
| 5,719,049 A | 2/1998 | Pellegrini et al. |
| 5,719,051 A | 2/1998 | Mundt et al. |
| 5,756,341 A | 5/1998 | Kistner et al. |
| 5,824,482 A | 10/1998 | Alizon et al. |
| 5,837,520 A | 11/1998 | Shabram et al. |
| 5,994,134 A | 11/1999 | Giroux et al. |
| 6,001,557 A | 12/1999 | Wilson et al. |
| 6,008,036 A | 12/1999 | Fanget et al. |
| 6,033,895 A | 3/2000 | Garger et al. |
| 6,037,165 A | 3/2000 | Montagnier et al. |
| 6,048,537 A | 4/2000 | Violay et al. |
| 6,080,571 A | 6/2000 | Prior et al. |
| 6,143,548 A | 11/2000 | O'Riordan et al. |
| 6,194,192 B1 | 2/2001 | Ueno et al. |
| 6,203,975 B1 | 3/2001 | Wilson et al. |
| 6,261,551 B1 | 7/2001 | Wilson et al. |
| 6,261,823 B1 | 7/2001 | Tang et al. |
| 6,306,637 B1 | 10/2001 | Ewasyshyn et al. |
| 6,316,185 B1 | 11/2001 | Saifer et al. |
| 6,358,744 B1 | 3/2002 | Volkin et al. |
| 6,383,794 B1 | 5/2002 | Mountz et al. |
| 6,387,368 B1 | 5/2002 | Wilson et al. |
| 6,410,300 B1 | 6/2002 | Samulski et al. |
| 6,528,305 B2 | 3/2003 | Thompson et al. |

(Continued)

FOREIGN PATENT DOCUMENTS

| | | |
|---|---|---|
| CN | 1228474 A | 9/1999 |
| EP | 1 501 921 B1 | 4/2009 |

(Continued)

OTHER PUBLICATIONS

European Biotechnology, "A solution to the challenges of downstream processing", European Biotechnology Life Science and Industry Magazine, Mar. 2010:pdf p. 1.*
Cabatingan, M., "Impact of Virus Stock Quality on Virus Filter Validation," *BioProcess International* 3(10):39-44 (2005).
Korneyeva, M., et al., "Important Parameters for Optimal Target Virus Clearance: Virus Spike Selection Issues," *American Pharmaceutical Review*, Russell Publ., (1):38-42.
O'Neil, P.F. and Balkovic, E.S., "Virus Harvesting and Affinity-Based Liquid Chromatography", *Bio/Technology* 11:173-178 (1993).
Segura, M.de las M., et al., "Downstream Processing of Oncoretroviral and Lentiviral Gene Therapy Vectors", *Biotechnology Advances* 24:321-337 (2006).

(Continued)

*Primary Examiner* — Janet L Andres
*Assistant Examiner* — Barry A Chestnut
(74) *Attorney, Agent, or Firm* — Hamilton, Brook, Smith & Reynolds, P.C.

(57) ABSTRACT

The purity and titer of virus stocks used for virus clearance studies have a significant influence on study outcome, and impact how well the scale-down model represents the production-scale process. Impurities in virus stocks are particularly important in the testing of small virus retentive filters because these impurities may cause a filter to foul prematurely, leading to underestimation of the true throughput capability of the filter and consequent inappropriate sizing of the production scale unit. In addition, impurities can also affect the levels of virus clearance observed by altering the fouling mechanisms and subsequent fluid passage through the virus filter. Described herein are methods for making, producing and using high purity virus stocks having high titer.

19 Claims, 9 Drawing Sheets

(56) References Cited

U.S. PATENT DOCUMENTS

| | | |
|---|---|---|
| 6,602,697 B1 | 8/2003 | Cook, III |
| 6,660,514 B1 | 12/2003 | Zolotukhin et al. |
| 6,686,190 B2 | 2/2004 | Lau |
| 6,709,811 B1 | 3/2004 | Evans et al. |
| 6,773,915 B2 | 8/2004 | Guertler et al. |
| 6,793,926 B1 | 9/2004 | Rasty et al. |
| 6,884,613 B2 | 4/2005 | LeDoux et al. |
| 6,951,752 B2 | 10/2005 | Reiter et al. |
| 6,989,264 B2 | 1/2006 | Atkinson et al. |
| 7,091,030 B2 | 8/2006 | Setiawan et al. |
| 7,195,905 B2 | 3/2007 | Kistner et al. |
| 7,223,585 B2 | 5/2007 | Coffey |
| 7,344,839 B2 | 3/2008 | Calton et al. |
| 7,378,265 B2 | 5/2008 | Gaillac et al. |
| 7,419,817 B2 | 9/2008 | Chiorini et al. |
| 2001/0001290 A1 | 5/2001 | Lau |
| 2001/0001709 A1 | 5/2001 | Lau |
| 2001/0034055 A1 | 10/2001 | Lee et al. |
| 2001/0036657 A1 | 11/2001 | Tang et al. |
| 2001/0043916 A1 | 11/2001 | McNeilly et al. |
| 2002/0028497 A1 | 3/2002 | Blanche et al. |
| 2002/0037576 A1 | 3/2002 | Thompson et al. |
| 2002/0081710 A1 | 6/2002 | LeDoux et al. |
| 2003/0013076 A1 | 1/2003 | Robinson et al. |
| 2003/0022356 A1 | 1/2003 | Leblois-Prehaud et al. |
| 2003/0053990 A1 | 3/2003 | Rabinowitz et al. |
| 2003/0108859 A1 | 6/2003 | Kistner et al. |
| 2003/0108860 A1 | 6/2003 | Reiter et al. |
| 2003/0124511 A1 | 7/2003 | Tauer et al. |
| 2003/0143730 A1 | 7/2003 | Blanche et al. |
| 2003/0166253 A1 | 9/2003 | Thompson et al. |
| 2004/0005693 A1 | 1/2004 | Coffey |
| 2004/0126869 A1 | 7/2004 | Thompson et al. |
| 2004/0152183 A1 | 8/2004 | O'Riordan et al. |
| 2004/0157310 A1 | 8/2004 | Lau |
| 2005/0003507 A1 | 1/2005 | Kostel et al. |
| 2005/0009168 A1 | 1/2005 | Robbins et al. |
| 2005/0019928 A1 | 1/2005 | Rasty et al. |
| 2005/0032044 A1 | 2/2005 | Setiwan et al. |
| 2005/0118698 A1 | 6/2005 | Vorlop et al. |
| 2005/0118701 A1 | 6/2005 | Zhou et al. |
| 2005/0153420 A1 | 7/2005 | Konz, Jr. et al. |
| 2005/0158712 A1 | 7/2005 | Leboulch et al. |
| 2005/0176146 A1 | 8/2005 | Xie et al. |
| 2005/0196854 A1 | 9/2005 | Konz, Jr. et al. |
| 2005/0214324 A1 | 9/2005 | Rathe et al. |
| 2005/0244942 A1 | 11/2005 | O'Riordan et al. |
| 2005/0260168 A1 | 11/2005 | Frei et al. |
| 2006/0035364 A1 | 2/2006 | Wright et al. |
| 2006/0088869 A1 | 4/2006 | Coffey |
| 2006/0188991 A1 | 8/2006 | McCormick et al. |
| 2006/0275781 A1 | 12/2006 | Pham et al. |
| 2006/0281075 A1 | 12/2006 | Smith et al. |
| 2007/0141561 A1 | 6/2007 | Kim et al. |
| 2007/0141617 A1 | 6/2007 | Kistner et al. |
| 2007/0155008 A1 | 7/2007 | Zhang et al. |
| 2007/0172846 A1 | 7/2007 | Zhang et al. |
| 2007/0207461 A1 | 9/2007 | Weggeman |
| 2007/0254352 A1 | 11/2007 | Schaffer et al. |
| 2007/0269856 A1 | 11/2007 | Coffey |
| 2007/0275449 A1 | 11/2007 | Wu et al. |
| 2008/0014626 A1 | 1/2008 | Pohlscheidt et al. |
| 2008/0050770 A1 | 2/2008 | Zhang et al. |
| 2008/0085545 A1 | 4/2008 | Frei et al. |
| 2008/0113336 A1 | 5/2008 | Transfiguracion et al. |
| 2008/0187546 A1 | 8/2008 | Wasmoen et al. |
| 2008/0194002 A1 | 8/2008 | Frei et al. |
| 2008/0213753 A1 | 9/2008 | Henning et al. |
| 2008/0241185 A1 | 10/2008 | Kofinas et al. |
| 2008/0254067 A1 | 10/2008 | Trepanier et al. |
| 2008/0274138 A1 | 11/2008 | Reiter et al. |
| 2008/0293123 A1 | 11/2008 | Frei et al. |
| 2008/0299545 A1* | 12/2008 | Zhang et al. ............. 435/5 |
| 2009/0123989 A1 | 5/2009 | Weggeman |

FOREIGN PATENT DOCUMENTS

| | | |
|---|---|---|
| JP | Hei-2-500166 | 1/1990 |
| JP | 2000-514290 | 10/2000 |
| JP | 2003-523169 A | 8/2003 |
| JP | 2006-514538 A | 5/2006 |
| WO | WO 98/22588 A2 | 5/1998 |
| WO | WO 2005/063970 A1 | 7/2005 |
| WO | WO 2007/127264 A2 | 11/2007 |
| WO | WO2007127264 * | 11/2007 |
| WO | WO 2008/026225 A2 | 3/2008 |
| WO | WO2008026225 * | 3/2008 |
| WO | WO2008113011 * | 9/2008 |
| WO | WO 2011/130119 A2 | 10/2011 |

OTHER PUBLICATIONS

Valera, C.R., et al., "Application of Multivirus Spike Approach for Viral Clearance Evaluation", *Biotechnol Bioeng* 84:714-722 (2003).

Communication with extended European Search Report, EP 11162488.8, mailed Jul. 19, 2011.

Asher, D.R., "Spike Right: Ultrapure Virus Preparations for Virus Filter Validation" presented at the International Society for BioProcess Technology, 2-day Conference: Ensuring Viral Safety and Clearance in Biologics: Nov. 30-Dec. 1, 2010.

Asher, D.R., "Spike Right: Ultrapure Virus Preparations for Virus Filter Validation", Abstract, IBC's 8th International Conference, Viral Safety for Biologicals, Feb. 24-25, 2011.

Asher, D.R., et al., "Predicting Virus Filtration Performance With Virus Spike Characterization", *BioProcess International*, pp. 26-37 (2011).

Asher, D.R., "Spike Right: Ultrapure Virus Preparations for Virus Filter Validation", Abstract, ISBioTech, 1st Annual Meeting, Apr. 4-6, 2011.

Kahn, N.Z., et al., "Filter preconditioning enables representative scaled-down modelling of filter capacity and viral clearance by mitigating the impact of virus spike impurities", *Biotechnol. Appl. Biochem.* 52:293-301 (2009).

International Preliminary Report on Patentability from counterpart International Application No. PCT/US2011/031747, "Methods of Producing High Titer, High Purity Virus Stocks and Methods of Use Thereof", dated Oct. 26, 2012.

Previsani, N., et al., "Growth of the Parvovirus Minute Virus of Mice MVMp3 in EL4 Lymphocytes is Restricted After Cell Entry and Before Viral DNA Amplification: Cell-Specific Differences in Virus Uncoating in Vitro," *J. Virol.* 71(10):7769-7780 (1997).

Notification of Transmittal of the International Search Report (ISR) and Written Opinion (WO) of the International Searching Authority with the ISR and WO, PCT/US2011/031747, entitled Methods of Producing High Titer, High Purity Virus Stocks and Methods of Use Thereof, dated Feb. 8, 2012.

"Converting TCID[50] to Plaque Forming Units (PFU). Is it Possible to Determine From the TCID[50] How Many Plaque Forming Units to Expect?" in ATCC—Converting TCID50 to Plaque Forming Units PFU-124, downloaded on Nov. 17, 2015 from URL: http://www.atcc.org/Global/FAQs/4/8/Converting%20TCID50%20to%20plaque%20form . . . , 1 page.

Hensgen, M.I., et al., "Purification of Minute Virus of Mice Using High Performance Tangential Flow Filtration", Desalination, 250(3):1121-1124 (2010).

Iyer, P., et al., "Comparison of Manufacturing Techniques for Adenovirus Production", Cytotechnology, 30:169-172 (1999).

Romanowski, P., et al., "Variable Affecting Titer and Long-Term Stability of Virus Stocks", BioProcess Technical, downloaded on Nov. 17, 2015 from URL: http://www.bioprocessintl.com/wp-content/plugins/pdfjs-viewer-shortcode/web/viewer.php?file . . . , 3 pages.

Schoofs, G., et al., "A High-Yeilding Serum-Free, Suspension Cell Culture Process to Manufacture Recombinant Adenoviral Vectors for Gene Therapy", Cytotechnology, 28:81-89 (1998).

Carter, J. and Saunders, V., "Quantal assay." In *Virology Principles and Applications*, John Wiley & Sons, Ltd, eds. (West Sussex, London), pp. 23-24 (2007).

* cited by examiner

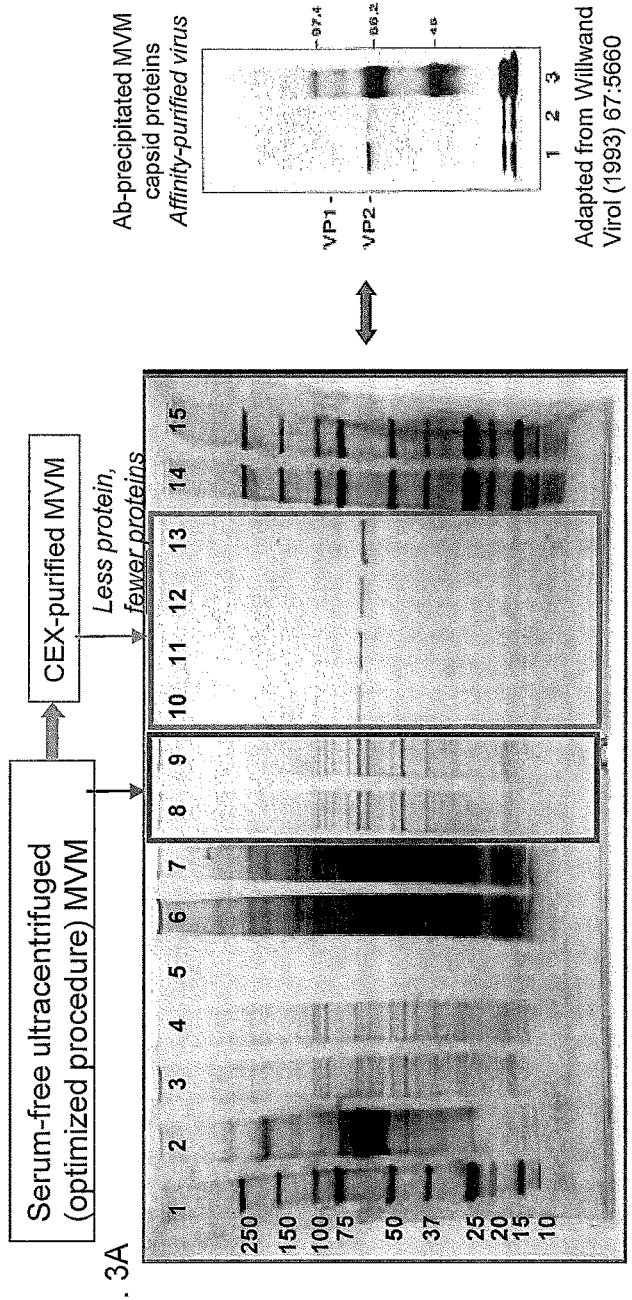
FIG. 3A
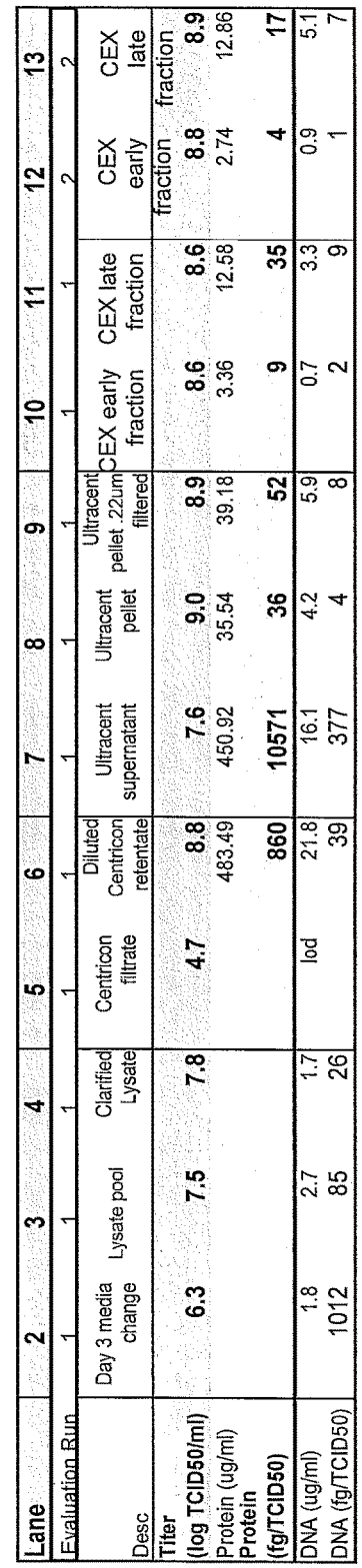
FIG. 3B
FIG. 3C

| Protocol Cellhost Format Eval run # | 324K T150 x 30 | | PROC-004 324K T150 x 30 1 | PROC-005 324K T150 x 30 2 | PROC-006 324K T150 x 30 3 | PROC-007 324K T150 x 30 4 |
|---|---|---|---|---|---|---|
| | AVERAGE | STD DEV | | | | |
| Clar lysate |  |  |  |  |  |  |
| Titer (log TCID50/ml) | 7.71 | ±0.06 | 7.70 | 7.63 | 7.75 | 7.75 |
| Centricon filtrate (discarded) |  |  |  |  |  |  |
| Titer (log TCID50/ml) | 4.52 | ±0.26 | 4.44 | 4.69 | 4.75 | 4.19 |
| Centricon retentate (diluted to 30ml) |  |  |  |  |  |  |
| Titer (log TCID50/ml) | 8.85 | ±0.24 | 8.75 | 8.81 | 9.19 | 8.63 |
| Protein (ug/ml) | 631.31 | ±209.04 | 483.49 |  | 779.12 |  |
| DNA (ug/ml) | 30.18 | ±11.85 | 21.80 |  | 38.56 |  |
| U/C Sup (discarded) |  |  |  |  |  |  |
| Titer (log TCID50/ml) | 7.27 | ±0.33 | 7.63 | 7.44 | 7.13 | 6.88 |
| Protein (ug/ml) | 561.68 | ±156.64 | 450.92 |  | 672.44 |  |
| DNA (ug/ml) | 20.95 | ±6.85 | 16.10 |  | 25.79 |  |
| Virus Loss | 3% |  | 8% | 4% | 1% | 2% |
| U/C Pellet |  |  |  |  |  |  |
| Titer (log TCID50/ml) | 8.75 | ±0.20 | 9.00 | 8.81 | 8.63 | 8.56 |
| Protein (ug/ml) | 43.11 | ±10.70 | 35.54 |  | 50.67 |  |
| DNA (ug/ml) | 6.41 | ±3.12 | 4.20 |  | 8.61 |  |
| CEX early fract |  |  |  |  |  |  |
| Titer (log TCID50/ml) | 8.66 | ±0.12 | 8.56 | 8.81 | 8.69 | 8.56 |
| Protein (ug/ml) | 8.27 | ±6.03 | 3.36 | 2.74 | 13.66 | 13.30 |
| Protein/virus (fg/TCID50) | 19.50 | ±15.29 | 9.25 | 4.24 | 27.89 | 36.63 |
| DNA (ug/ml) | 0.94 | ±0.43 | 0.70 | 0.90 | 1.55 | 0.59 |
| DNA (fg/TCID50) | 2.03 | ±0.79 | 1.93 | 1.39 | 3.16 | 1.62 |
| CEX late fract |  |  |  |  |  |  |
| Titer (log TCID50/ml) | 8.82 | ±0.07 | 8.73 | 8.88 | 8.88 | 8.81 |
| Protein (ug/ml) | 21.23 | ±10.59 | 12.58 | 12.86 | 24.90 | 34.58 |
| Protein/virus (fg/TCID50) | 31.74 | ±15.94 | 23.61 | 16.95 | 32.82 | 53.56 |
| DNA (ug/ml) | 6.15 | ±2.70 | 3.30 | 5.10 | 6.52 | 9.68 |
| DNA (fg/TCID50) | 9.13 | ±4.04 | 6.19 | 6.72 | 8.60 | 14.99 |
| Total Virus Harvest |  |  |  |  |  |  |
| log TCID50 | 10.46 | ±0.06 | 10.45 | 10.38 | 10.50 | 10.50 |
| Total Virus Yield |  |  |  |  |  |  |
| log TCID50 | 10.22 | ±0.09 | 10.12 | 10.32 | 10.26 | 10.16 |
| Purification Loss |  |  |  |  |  |  |
| log TCID50 | 0.24 | ±0.13 | 0.33 | 0.06 | 0.24 | 0.34 |

FIG. 4

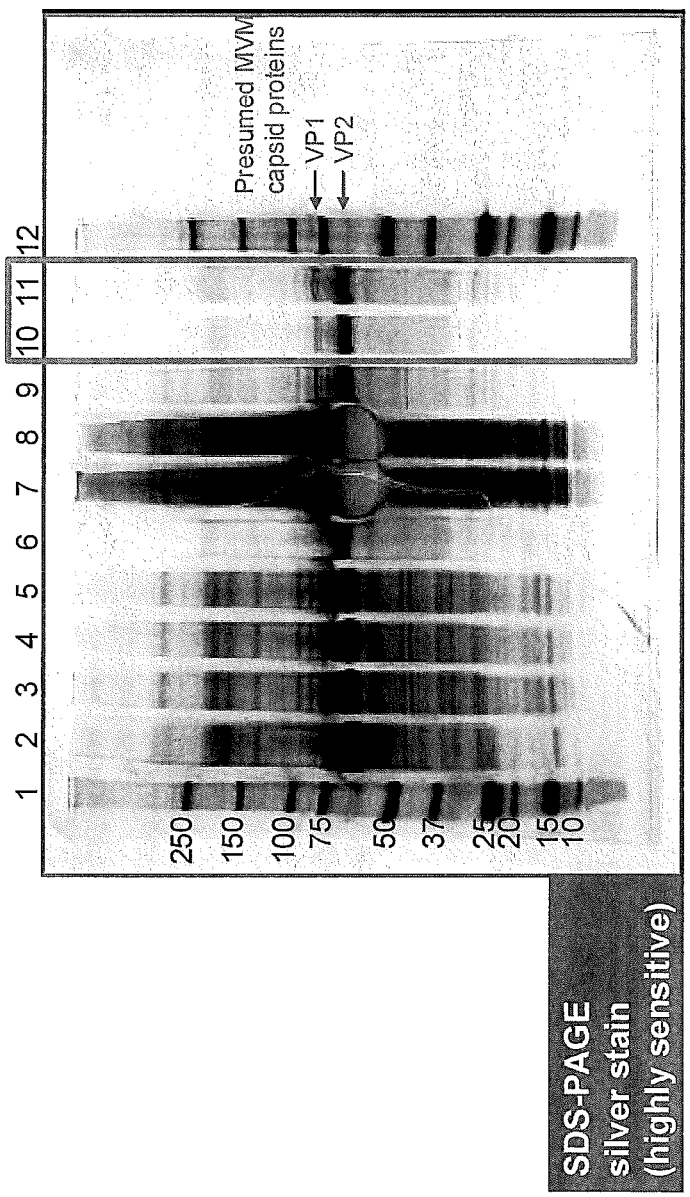
| Lane | 2 | 3 | 4 | 5 | 6 | 7 | 8 | 9 | 10 | 11 |
|---|---|---|---|---|---|---|---|---|---|---|
| Desc | Media change | Lysate pool | Clarified lysate | Clarified lysate | Centricon filtrate | Centricon retentate (diluted) | Ultracent Supernatant | Resusp pellet | Scrubbed fract 3 | Scrubbed fract 27 |
| Titer (log TCID50/ml) | 6.7 | 9.8 | 9.9 | 9.9 | 6.7 | 10.3 | 9.2 | 10.6 | 10.6 | 10.3 |
| Protein (ug/ml) | | | | | | 9856 | 9366 | 135 | 94 | 105 |
| Protein (fg/TCID50) | 0 | 0 | 0 | 0 | 0 | 483 | 6047 | 4 | 2 | 5 |
FIG. 5A
FIG. 5B

|  |  | Protocol | PROC-010 |
|---|---|---|---|
|  |  | Cellhost | A9 |
|  |  | Format | T150 x 30 |
|  |  | Eval run # | 5 |
| Clar lysate | Titer (log TCID50/ml) |  | 9.88 |
| Centricon filtrate (discarded) | Titer (log TCID50/ml) |  | 6.69 |
| Centricon retentate (diluted to 30ml) | Titer (log TCID50/ml) |  | 10.31 |
|  | Protein (ug/ml) |  | 9856.00 |
| U/C Sup (discarded) | Titer (log TCID50/ml) |  | 9.19 |
|  | Protein (ug/ml) |  | 9366.00 |
|  | Virus Loss |  | 8% |
| U/C Pellet | Titer (log TCID50/ml) |  | 10.56 |
|  | Protein (ug/ml) |  | 134.56 |
| CEX early fract | Titer (log TCID50/ml) |  | 10.63 |
|  | Protein (ug/ml) |  | 93.63 |
|  | Protein/virus (fg/TCID50) |  | 2.19 |
| CEX late fract | Titer (log TCID50/ml) |  | 10.31 |
|  | Protein (ug/ml) |  | 104.90 |
|  | Protein/virus (fg/TCID50) |  | 5.14 |
| Total Virus Harvest | log TCID50 |  | 12.63 |
| Total Virus Yield | log TCID50 |  | 11.98 |
| Purification Loss | log TCID50 |  | 0.65 |

FIG. 6

METHODS OF PRODUCING HIGH TITER, HIGH PURITY VIRUS STOCKS AND METHODS OF USE THEREOF

RELATED APPLICATION

This application claims the benefit of U.S. Provisional Application No. 61/324,220, filed on Apr. 14, 2010. The entire teachings of the above application are incorporated herein by reference.

BACKGROUND OF THE INVENTION

Biopharmaceutical products, such as monoclonal antibodies, recombinant proteins, vaccines, blood derivatives and animal products carry a risk of transmitting infectious viruses. This is due to source material possibly being intrinsically contaminated with viruses. Additionally, manufacturing processes of biopharmaceutical products are susceptible to virus contamination from extrinsic sources. As a result, manufacturers of biopharmaceutical products are required to incorporate sufficient virus clearance steps into their manufacturing processes to ensure that their products are contaminant virus-free. It is a safety and regulatory imperative that manufacturing processes of biopharmaceutical products incorporate these virus clearance steps.

Evaluation of virus clearance step effectiveness in the manufacturing process is necessary. The purpose of virus clearance evaluation is to assess the capability of a manufacturing production process to inactivate and/or remove potential virus contaminants. Spiking studies are typically used to evaluate and validate virus clearance steps in a scaled down model of a production-scale process. However, the purity and titer of virus stocks used for virus clearance studies have a significant influence on study outcome. The purity and titer of the virus stocks impact how well the scaled down model represents the production-scale process.

For example, impurities in virus stocks adversely impact the testing of small virus retentive filters used in virus clearance steps. The impurities are introduced as a consequence of the impure virus stock used in the validating spiking studies, and are not reflective of typical manufacturing processes on the production-scale process. As a result of the impurities, the test unit (e.g., a filter) fouls prematurely, exhibits altered fouling conditions, and adversely affects fluid passage through the virus filter. Consequently, the true throughput capacity of the filter is underestimated, which in turn leads to the inappropriate sizing of the production scale-unit. As a result, the production-scale unit is oversized to compensate for the apparent lower performance of the unit in the validation study. This increases production costs. In addition, this underestimates the actual capacity of the test unit to clear virus in the production process since the titer of the virus stock often determines the maximum possible concentration of virus spiked into the test material which, when all virus is effectively cleared by the test unit, limits the virus clearance claim of the test unit.

Current methods of producing virus stocks (e.g., for use in spiking studies) lack the capacity to produce virus stocks with low impurity content. Furthermore, virus stocks of as high titer as possible are desirable, since the volume of virus spike that can be added to a test system is limited by Regulatory Guidelines. Current methods lack the capacity to produce virus stocks of high titer and high purity. Thus, a need exists for methods of preparing virus stocks with high purity, as well as high titer.

SUMMARY OF THE INVENTION

Described herein are methods of producing high purity virus stocks, as well as the virus and virus stocks produced by the methods. The virus can be any suitable virus as desired, such as a mammalian virus, or a bacteriophage. Such virus stocks are suitable for use, for example, as a virus spike in an evaluation and/or validation study.

Thus, one embodiment of the invention is a method of preparing a high purity virus. The method comprises the sequential steps of obtaining a viral sample prepared under low protein conditions, concentrating the viral sample in a suitable buffer, and precipitating the virus in the viral sample, such that the precipitated virus is a high purity virus. In one embodiment, the high purity virus is a high purity virus stock solution.

In another embodiment of the invention, the method of preparing a high purity virus comprises chromatographic polishing. In one embodiment, the method of preparing a high purity virus comprises the sequential steps of obtaining a viral sample prepared under low protein conditions, concentrating the viral sample in a suitable buffer, precipitating the virus in the viral sample, and chromatographic polishing the precipitated virus, thereby producing a high purity virus. In one embodiment, the high purity virus is a high purity virus stock solution.

In one embodiment, the high purity virus or high purity virus stock solution has a protein concentration of less than 50 ug/ml. In another embodiment, the high purity virus or high purity virus stock solution has a protein concentration of less than 100 fg/TCID$_{50}$. In one embodiment, the high purity virus or high purity virus stock solution has a protein concentration of less than 60 fg/TCID$_{50}$. In another embodiment, the high purity virus or high purity virus stock solution has a DNA concentration of less than 50 fg/TCID$_{50}$. In one embodiment, the high purity virus or high purity virus stock solution has a DNA concentration of less than 15 fg/TCID$_{50}$.

In a further embodiment, the high purity virus or high purity virus stock solution has a protein concentration of less than 100 fg/TCID$_{50}$ and a DNA concentration of less than 50 fg/TCID$_{50}$. In one embodiment, the high purity virus or high purity virus stock solution has a protein concentration of less than 60 fg/TCID$_{50}$ and a DNA concentration of less than 15 fg/TCID$_{50}$.

In a further embodiment, the high purity virus or high purity virus stock solution has a virus concentration of at least $10^6$ TCID$_{50}$/ml.

A further embodiment of the invention is a method of evaluating and/or validating a virus clearance process and materials used therein. A scaled virus clearance process is tested using the test sample and analyzing the results of the virus clearance process. The amount of virus clearance evaluates and determines the validation of the virus clearance process and the materials used in the virus clearance process. If the virus is sufficiently removed from the test sample to meet regulatory standards, the virus clearance process and materials used in the clearance process are validated.

In one embodiment, the method of evaluating and/or validating a virus clearance process comprises spiking a sample with a high purity virus stock solution to produce a test sample. In one embodiment, the high purity virus solution comprises a protein concentration of less than 100 fg/TCID$_{50}$, and a DNA concentration of less than 50 fg/TCID$_{50}$.

Another embodiment of the invention is a method of evaluating and/or validating a virus clearance process in a method comprising spiking a sample with a virus solution, wherein the virus solution is prepared by a method comprising flow-through chromatography, a bead-based chromatography, size-exclusion processing, or hydrophobicity-based processing. In one embodiment, the virus solution is prepared by cation exchange flow-through chromatography. In another embodiment, the virus solution is prepared by anion exchange flow-through chromatography. In one embodiment, the flow-through chromatography comprises cation exchange flow-through chromatography on a membrane or a bead-based matrix.

In one embodiment, the method of evaluating and/or validating a virus clearance process and materials used therein comprises spiking a sample with a high purity virus stock solution comprising at least $10^7$ $TCID_{50}$/ml of virus, a protein concentration of less than 100 fg/$TCID_{50}$, and a DNA concentration of less than 50 fg/$TCID_{50}$.

BRIEF DESCRIPTION OF THE DRAWINGS

FIGS. 3A-3C illustrate one embodiment of the invention.

FIG. 3A is a silver-stained SDS-PAGE gel of samples taken at different stages in a sample virus preparation process. Lanes 1, 14 and 15 are standard molecular weight markers. Lane 2 is a sample of the MVM infected cell media at day 3 immediately before the changing of the media from Dulbecco's Modified Eagle Medium (DMEM) with 1% fetal bovine serum (FBS) to serum-free DMEM. Lane 3 is a sample of pooled cell lysate at the completion of infection on day 14. Lane 4 is a sample of clarified lysate. Lane 5 is a sample of filtrate from ultrafiltration (CENTRICON®) (a centrifugal filter unit) for virus concentration. Lane 6 is a sample of diluted retentate from ultrafiltration for virus concentration. Lane 7 is a sample of supernatant after virus precipitation by ultracentrifugation. Lane 8 is a sample of the virus pellet after virus precipitation by ultracentrifugation. Lane 9 is a sample of the virus pellet after virus precipitation by ultracentrifugation and filtration through a 0.22 micron filter. Lanes 10 and 12 are samples of an early fraction of chromatographic polishing using a cationic exchange (CEX) membrane adsorber comprising AMPS (2-Acrylamido-2-methyl-1-propanesulfonic acid) cross-linked by MBAm (N,N'-methylenebisacrylamide) on a poly ether sulphone (PES) matrix. Lanes 11 and 13 are late fractions of chromatographic polishing using the CEX membrane adsorber.

FIG. 3B is adapted from Willwand et al., J Virol (1993) 67:5660 demonstrating the molecular sizes of MVM capsid proteins VP1 is 83 kDa and VP2 is 64 kDa. The predominant two protein bands apparent by silver-stained SDS-PAGE in the final purified virus product (FIG. 3A) are of the same size and in the same proportion as known MVM virus capsid proteins VP1 and VP2, suggesting a very pure virus stock in which the major remaining proteins are viral rather than impurities.

FIG. 3C is a table corresponding to the SDS-PAGE gel in FIG. 3A with calculated MVM virus titers (log $TCID_{50}$/ml), protein concentrations (ug/ml and fg/$TCID_{50}$), and DNA concentrations (ug/ml and fg/TCID50) for each sample in lanes 2-13.

FIG. 4 is a table demonstrating the reproducibility of the MVM production process described herein.

FIGS. 5A-5B illustrate one embodiment of the invention.

FIG. 5A is a table corresponding to the SDS-PAGE gel in FIG. 5B with calculated MVM virus titers (log $TCID_{50}$/ml) and protein concentrations (ug/ml and fg/TCID50) for each sample in lanes 2-11.

FIG. 5B is a silver-stained SDS-PAGE gel of samples taken at different stages in a sample virus preparation process. Lanes 1 and 12 are standard molecular weight markers. Lane 2 is a sample of the MVM infected cell media at day 3 immediately before the changing of the media from Advanced™ DMEM with 1% FBS to serum-free Advanced™ DMEM. Lane 3 is a sample of pooled cell lysate at the completion of infection on day 14. Lanes 4 and 5 are samples of clarified lysate. Lane 6 is a sample of filtrate from ultrafiltration (CENTRICON®) (a centrifugal filter unit) for virus concentration. Lane 7 is a sample of diluted retentate from ultrafiltration for virus concentration. Lane 8 is a sample of supernatant after virus precipitation by ultracentrifugation. Lane 9 is a sample of the virus pellet resuspended after virus precipitation by ultracentrifugation. Lane 10 is a sample of the third fraction of chromatographic polishing using CEX membrane adsorber. Lane 11 is a sample of the twenty-seventh fraction of chromatographic polishing using CEX membrane adsorber.

FIG. 6 is a table of data for virus production of high titer and high purity, using the methods as described herein.

DETAILED DESCRIPTION OF THE INVENTION

Figure 1:
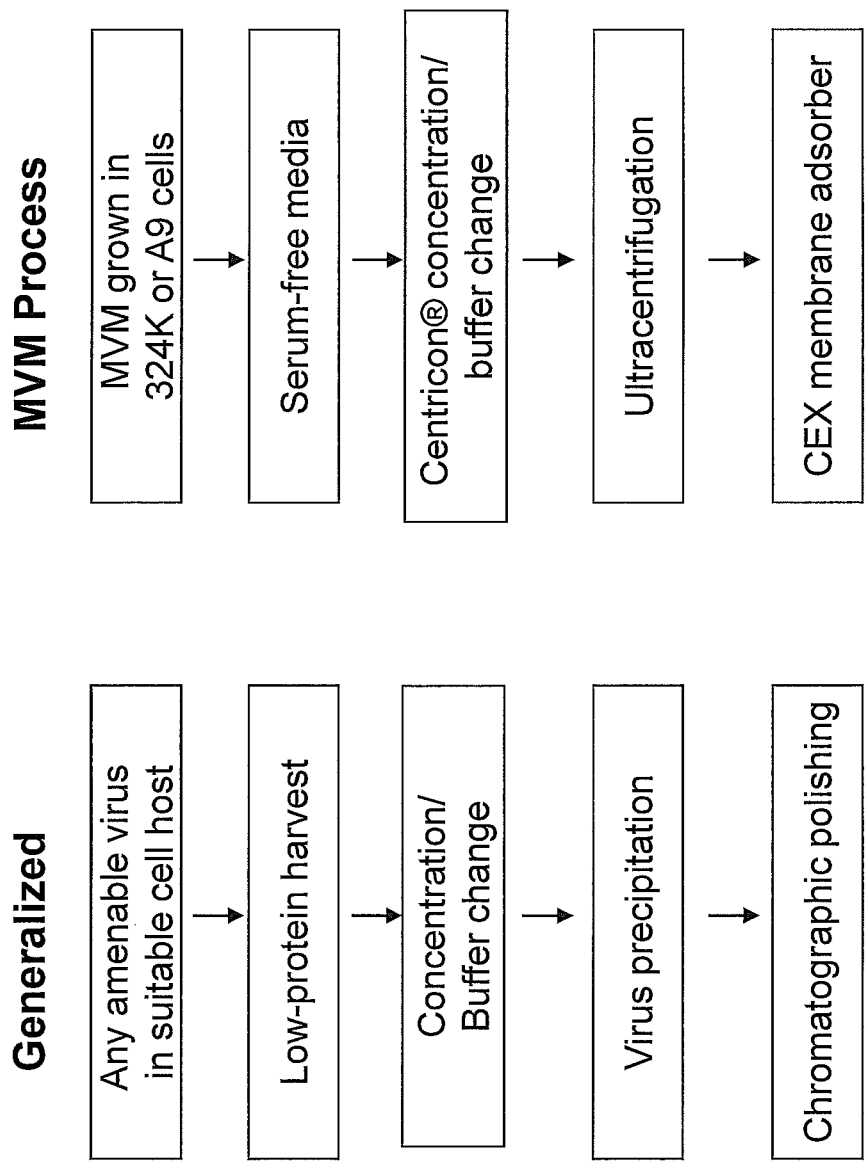
FIG. 1 is a schematic outline of the generalized virus production protocol and an example of a specific minute virus of mice (MVM) production process.

Contamination of biopharmaceutical products, e.g., antibodies, recombinant proteins, vaccines, blood derivatives, plasma, and animal products, etc., by bacteria, viruses, prions, and the like, is a serious risk that needs to be sufficiently addressed. Contamination can arise by different ways. For example, it can occur because the source material (e.g., the cells in a cell culture, the blood product, etc.) is intrinsically contaminated with viruses. The manufacturing processes of biopharmaceutical products are also susceptible to virus contamination from extrinsic sources (e.g., inadvertent introduction from use of non-sterile or improperly sterilized materials). Because of the nature of the products, manufacturers of biopharmaceutical products are highly regulated and are required to incorporate sufficient virus clearance steps into their manufacturing processes to ensure that their products are contaminant-free. Multiple virus clearance steps can be incorporated into a manufacturing process. Each of these virus clearance steps needs to be evaluated for its effectiveness and thus, validated before a biopharmaceutical manufacturing process is approved. Virus clearance steps typically involve either virus removal steps or virus inactivation steps.

Virus removal is a method in which the virus is physically removed from the sample. This is often achieved by either nanofiltration or chromatography. Nanofiltration techniques remove viruses by size exclusion. The success of chromatographic methods for removing viruses depends on the column composition and the reagents (e.g., buffers) used.

Virus inactivation is a method in which the viruses may remain in the final product, but in a non-infective (inactive) form. Many viruses contain lipid or protein coats that can be inactivated by chemical alteration. Alternatively, some viral inactivation processes denature the virus completely. Examples of virus inactivation methods include solvent and/or detergent inactivation, pasteurization (e.g., heating to high temperatures), pH inactivation (e.g., using an acidic pH), and irradiation (e.g., ultraviolet (UV) or gamma irradiation).

The concentration of a contaminating virus, or the risk of virus contamination, in a manufacturing process may be extremely low, but, because viruses are by their nature infective, even one viral particle can be sufficient to ruin an entire run in a manufacturing process. It is for this reason that special measures must be taken to determine the appropriate removal or inactivation methods in a manufacturing process. As such, the effectiveness of such virus clearance methods needs to be evaluated and validated. Spiking studies were created specifically for this purpose.

Spiking studies use a scaled down model of the virus clearance step of a production-scale process to evaluating and/or validate the virus clearance steps and to evaluating and/or validate the apparatus used in the virus clearance method. The purity and titer of the virus stocks impact how well the scaled down model represents the production-scale process. Impurities (e.g., DNA, RNA, protein, lipids, non-infectious particles and virus aggregates) in virus stocks adversely affect the results of spiking studies. For example, impurities can alter virus clearance rates by blocking the action of virus-inactivating chemicals, block effectiveness of radiation, alter binding to chromatographic media of target agents (e.g., inappropriate inhibition of binding or inappropriate increase in binding to the chromatographic media), or by fouling (e.g., blocking or clogging) of filters. When a test unit (e.g., a filter or chromatography medium) fouls prematurely, or exhibits altered fouling characteristics, it ultimately reduces the passage of fluid through the virus filter. As a result, the actual throughput capacity of the filter is underestimated because such impurities are not normally present in the production-scale unit. Consequently, the production-scale unit is oversized to compensate for the apparent lower performance of the unit in the validation study. Current industry standard methods of producing virus stocks (e.g., for use in spiking studies) generally produce virus stocks with high impurity content.

In addition, virus stocks of as high a titer as possible are also desirable. This is in part because the volume of virus spike that can be added to a test system is limited by Regulatory Guidelines. The titer of the virus stock therefore determines the maximum possible concentration of virus spiked into the test material. As a result, the actual capacity of the test unit to clear virus in the production process may be underestimated. Current methods lack the capacity to produce virus stocks of high purity and high titer.

The virus preparation methods described herein produce virus of exceptionally high purity and high titer. These clean virus stocks are designed to enable high-concentration spiking in virus clearance studies without impacting the performance of the scaled-down unit operation. This is particularly useful for evaluation and validation of small virus retentive filters, which can be sensitive to virus stock impurities, particularly when combined with certain feed materials. In addition, higher virus titers allow larger virus reduction factors to be demonstrated and allow a more rigorous challenge to the virus clearance unit operation.

Exemplary viruses for use in virus clearance studies and which can be produced in high titer and with high purity using the methods described herein include mammalian viruses and bacteriophages, for example and without limitation: RNA enveloped viruses (e.g., retroviruses such as human immunodeficiency virus-1 (HIV-1), human immunodeficiency virus-2 (HIV-2), simian immunodeficiency virus (SIV), xenotropic, amphotropic, and ecotropic recombinant murine retroviruses, such as xenotropic murine leukemia virus (X-MuLV), visna virus; flaviviruses such as bovine viral diarrhea virus (BVDV); rhabdoviruses such as vesicular stomatitis virus (VSV); paramyxoviruses such as parainfluenza type 3 (PIV3)); RNA non-enveloped viruses (e.g., reoviruses such as reovirus type 3 (reo-3); picornaviruses such as poliovirus type 1 (PV-1); picornaviruses such as encephalomyocarditis (EMC) virus and hepatitis A virus (HAV)); DNA enveloped viruses (e.g., herpesviruses such as pseudorabies virus (PRV), infectious bovine rhinotracheitis (IBR) virus, and herpes simplex virus type 1 (HSV-1); poxviruses such as orf virus); DNA non-enveloped viruses (e.g., adenoviruses such as human adenovirus; polyomavirus, such as simian virus 40 (SV40), and parvovirus, such as porcine parvovirus (PPV), canine parvovirus (CPV), parvovirus B19, and minute virus of mice (MVM) (also known as mice minute virus, murine minute virus, MMV)); and bacteriophage such as Phi-X 174 (or Phi-X), pseudomonas phage PP7, enterobacteria phage PR772, and pseudomonas phage Phi-6.

The process described has been successfully applied to minute virus of mice (MVM). This parvovirus, being among the smallest and hardest to remove or inactivate viruses, is a "gold standard" for virus clearance, particularly for virus filtration of biopharmaceutical products. Therefore, this method is also applicable to other viruses, particularly those similar in nature to MVM (e.g., non-enveloped viruses produced by cells at relatively high titer). For example, porcine parvovirus (PPV), an important gold standard virus for the plasma industry, is structurally very similar to MVM.

For practical reasons, the process steps to be evaluated and validated are scaled down. This is because it would be impractical to use the actual production scale for the virus clearance study due to the volumes of virus needed in a virus spiking test. Furthermore, as will be readily apparent, it would be inappropriate to introduce infectious virus into the current good manufacturing practice (cGMP) manufacturing facility itself for testing. Virus clearance is calculated by comparing the viral load of the spiked starting material with the post-processing material obtained from the test unit to obtain the viral reduction factor (also referred to herein as the "virus reduction factor" or "VRF").

The generalized procedure for virus production of high purity and high titer, as well as a specific virus purification technique used for MVM, are schematically represented in FIG. 1.

One embodiment of the invention is a method of preparing a high purity virus or high purity virus stock solution. As used herein, a "high purity virus" is a virus which has a very low impurity (e.g., protein, DNA, lipid) concentration. In one embodiment, a high purity virus has a protein concentration of less than 50 ug/ml, less than 45 ug/ml, less than 40 ug/ml, less than 35 ug/ml, less than 30 ug/ml, less than 25 ug/ml, less than 20 ug/ml, less than 15 ug/ml, less than 10 ug/ml, less than 5 ug/ml, or less.

In another embodiment, the high purity virus or high purity virus stock solution has a protein concentration of less than 100 fg/$TCID_{50}$, less than 90 fg/$TCID_{50}$, less than 80 fg/$TCID_{50}$, less than 70 fg/$TCID_{50}$, less than 60 fg/$TCID_{50}$, less than 50 fg/$TCID_{50}$, less than 40 fg/$TCID_{50}$, less than 30 fg/$TCID_{50}$, less than 20 fg/$TCID_{50}$, less than 10 fg/$TCID_{50}$, less than 5 fg/$TCID_{50}$, or less.

In a further embodiment, the high purity virus or high purity virus stock solution has a DNA concentration of less than 50 fg/$TCID_{50}$, less than 45 fg/$TCID_{50}$, less than 40 fg/$TCID_{50}$, less than 35 fg/$TCID_{50}$, less than 30 fg/$TCID_{50}$, less than 25 fg/$TCID_{50}$, less than 20 fg/$TCID_{50}$, less than 15 fg/$TCID_{50}$, less than 10 fg/$TCID_{50}$, less than 5 fg/$TCID_{50}$, less than 1 fg/$TCID_{50}$, less than 0.5 fg/$TCID_{50}$, or less.

In a still further embodiment, the high purity virus or high purity virus stock solution has a protein concentration as defined above and a DNA concentration as defined above. In one embodiment, the high purity virus or high purity virus stock solution has a protein concentration of less than 100 fg/$TCID_{50}$ and a DNA concentration of less than 50 fg/$TCID_{50}$. In another embodiment, the high purity virus or high purity virus stock solution has a protein concentration of less than 60 fg/$TCID_{50}$ and a DNA concentration of less than 15 fg/$TCID_{50}$. In a further embodiment, the high purity virus or high purity virus stock solution has a protein concentration of less than 5 fg/$TCID_{50}$ and a DNA concentration of less than 0.5 fg/$TCID_{50}$.

As will be appreciated by a person of skill in the art, $TCID_{50}$/ml is a measurement of the amount of a pathogenic agent that will produce pathological change in 50% of cell cultures inoculated with the pathogenic agent, expressed as the "tissue culture infectious dose 50" ($TCID_{50}$). Techniques for determining $TCID_{50}$ values are known in the art. In general, serial dilutions of a virus stock are prepared and inoculated onto replicate cell cultures, for example, in multi-well formats (e.g., 96 well plastic plates). The number of cell cultures that are infected is then determined for each virus dilution after a period of cell culture, typically by looking for cytopathic effect (CPE). In a typical study, at high serial dilutions of virus, none of the cell cultures are infected because no particles are present. At low serial dilutions of virus, every cell culture is infected. When half of the cell cultures show a cytopathic effect at a particular serial dilution of virus, this is the dilution of virus at which 50% of the cell cultures are infected. This number can be calculated from the data and expressed as 50% tissue culture infectious dose ($TCID_{50}$) per milliliter.

In one embodiment, the virus stock has a virus concentration of at least, or at least about, $10^5$ $TCID_{50}$/ml, $5 \times 10^5$ $TCID_{50}$/ml, $10^6$ $TCID_{50}$/ml, $5 \times 10^6$ $TCID_{50}$/ml, $10^7$ $TCID_{50}$/ml, $5 \times 10^7$ $TCID_{50}$/ml, $10^8$ $TCID_{50}$/ml, $5 \times 10^8$ $TCID_{50}$/ml, $10^9$ $TCID_{50}$/ml, $5 \times 10^9$ $TCID_{50}$/ml, $10^{10}$ $TCID_{50}$/ml, $5 \times 10^{11}$ $TCID_{50}$/ml, $10^{11}$ $TCID_{50}$/ml, $5 \times 10^{11}$ $TCID_{50}$/ml, or more.

The method comprises the sequential steps of obtaining a viral sample prepared under low protein conditions, concentrating the viral sample, changing to a suitable buffer, and precipitating the virus in the viral sample, such that the precipitated virus is a high purity virus. In one embodiment, the high purity virus has a virus titer as described above.

A viral sample prepared under low protein conditions can be achieved using any suitable method. For example, the viral sample can be obtained from virus-infected cells cultured in low serum, serum-free, defined media culture, or a combination thereof. In one embodiment, the cells are infected in a low serum containing cell culture medium (e.g., Dulbecco's Modified Eagle's Medium (DMEM) with 1% fetal bovine serum (FBS)) and subsequently cultured in serum-free cell culture media (e.g., DMEM without FBS, or Advanced DMEM without FBS), or defined serum-free cell culture media. In another embodiment, the cells are infected in a serum-free cell culture media (e.g., DMEM without FBS, or Advanced DMEM without FBS), or defined serum-free cell culture media.

The virus is concentrated and the cell media exchanged for a suitable buffer. For example, the virus is concentrated in a suitable buffer such as Tris-NaCl-EDTA (TNE) buffer (e.g., 10 mM Tris, pH 8.0, 150 mM NaCl, 1 mM EDTA); phosphate buffered saline (PBS) buffer (e.g., 137 mM NaCl, 2.7 mM KCl, 100 mM $Na_2HPO_4$, 2 mM $KH_2PO_4$, pH 7.4); Tris buffered saline (TBS) (e.g., 50 mM Tris, 150 mM NaCl, pH pH 7.6); Tris-EDTA (TE) buffer (e.g., 10 mM Tris, 1 mM EDTA); or 10 mM Tris.

In one embodiment, the viral sample is concentrated by ultrafiltration (e.g., an ultrafiltration centrifugal device), tangential flow filtration, dialysis, or a combination thereof. In ultrafiltration, the sample is processed through a membrane that passes the fluid and small molecules (e.g., salts, sugars, and proteins with a diameter less than the pore size of the membrane) but retains the virus. The fluid can be driven through the ultrafiltration membrane by a number of methods, including, but not limited to, centrifugation, peristaltic pumping, vacuum and air pressure. The virus is then resuspended into the desired volume of a new buffer. In tangential flow filtration (also known as cross flow filtration), the feed solution flows perpendicular to the surface on an ultrafiltration membrane. A transmembrane pressure differential is created that causes fluid and small molecules to flow across the membrane while virus does not pass through, reducing the volume in the sample. The buffer can then be changed by feeding the new buffer into the tangential flow filtration system while continuing to draw fluid across the membrane. In dialysis, the sample is placed within a membrane sack that allows the free passage of fluid and small molecules but retains the virus in the interior. By placing this "dialysis bag" into a large volume of buffer with a defined osmolarity, the cell culture media in the sample is diluted into the new buffer and the volume within the bag is reduced, achieving both buffer exchange and concentration of the virus. In a particular embodiment, the viral sample is concentrated by ultrafiltration and buffer exchange to TNE.

Precipitating the virus in the viral sample can be achieved by any suitable method. For example, ultracentrifugation, chemical-induced precipitation, chromatographic binding, polymer-induced aggregation, or a combination thereof. Ultracentrifugation techniques are standard in the art. For example, viral samples can be ultracentrifuged using standard devices at about 4° C., at least about 25,000 RPM (112600×g), for at least about 4 hr and collected as a pellet at the bottom of the tube. A "cushion" of dense medium (e.g., glycerol) may be placed at the bottom of the tube before adding the sample so that the virus must pass through this dense layer to pellet at the bottom of the tube while impurities do not pass. Virus can also be centrifuged through a density gradient medium, such as cesium chloride or iodixanol, and the virus collected as a concentrated layer at some point along that density gradient. Virus precipitation using chemical agents can be any agent that binds the virus and forms insoluble aggregates (e.g., polyethylene glycol (PEG) of any suitable molecular weight (MW), such as about MW 6,000 to about MW 10,000). Chromatographic binding can be achieved by using a chromatographic medium that is suited to binding virus (e.g., Q- or S-type chemistry on agarose, controlled pore glass or membrane media). Soluble polymers that inducibly aggregate can also be used to precipitate virus in the virus sample (e.g., a smart polymer, such as polyethylene, polyvinyl chloride, polystyrene, polypropylene, and polyvinyl alcohol). In one embodiment, the virus is precipitated by ultracentrifugation.

In one embodiment, the method further comprises chromatographic polishing of the precipitated virus. As used herein, "chromatographic polishing" refers to removing trace impurities by passing the sample through a medium that retains impurities on the basis of their electrostatic charge or hydrophobicity, while the majority of virus passes through. Chromatographic polishing typically removes impurities not removed by virus precipitation. In one embodiment, the virus is subjected to flow-through chromatographic polishing (e.g., using a cationic exchange (CEX) membrane adsorber, or an anionic exchange medium, such as ChromaSorb™). Such chromatographic polishing removes impurities such as proteins, nucleic acids, lipids, and sugars on the basis of their electrostatic charge from the viral sample. Other chromatographic polishing methods can be used, for example other membrane absorbers (e.g., Pall Mustang S); bead-based chromatographic media with appropriate chemistry (S or Q depending on the virus and buffer conditions); size-exclusion media; hydrophobicity-based media). As will be appreciated by the skilled artisan, the choice of chromatographic polishing device to use is dependent upon the nature of the virus to be purified, the contaminants to be removed, and the scale of the purification.

In one embodiment of the methods described herein, the virus flows through the chromatographic polishing media without binding while impurities bind the media, and are thus removed from the sample. The buffer conditions may be adjusted (e.g., to change salt content and/or the pH value) to maximize virus passage and impurity removal. In one embodiment, MVM in THE buffer, pH 7, is passed through a cationic exchange (CEX) membrane adsorber device, causing protein and DNA impurities to be adsorbed to the membrane and be removed while the majority of the virus passes through.

In another embodiment, chromatographic polishing is applied to any method of virus preparation and purification to purify the virus and produce a high purity virus. For example, other methods for virus preparation and purification, in addition to those described herein, which can be further purified by chromatographic polishing include virus prepared by ultracentrifugation pelleting, gradient purification, ultrafiltration. Chromatographic polishing can also be used to purify virus from an unpurified virus preparation treated only by clarification to remove cellular debris. Such virus preparations may be purified, for example, in a flow-through mode using chromatographic media appropriate for the specific virus used, buffer conditions, and scale of the process. In one embodiment, a virus (e.g., MVM) concentrated by ultracentrifugation pelleting is passed through a cationic exchange (CEX) membrane. In one embodiment, the CEX membrane comprises AMPS (2-Acrylamido-2-methyl-1-propanesulfonic acid) crosslinked by MBAm (N,N'-methylenebisacrylamide) on a poly ether sulphone (PES) matrix. Virus (e.g., MVM) passes through the membrane without significant binding while impurities such as protein and DNA bind the membrane and are removed from the virus sample.

The methods described herein significantly reduce the presence of impurities in the virus stock. For example, the total amount of impurities in the virus stock is significantly reduced. By "total amount of impurities" it is meant that the quantity of impurities is reduced (e.g., the number of micrograms or femtograms of impurities such as protein, DNA, and the like, is reduced by about 90 to about 99% as determined by standard assays, e.g., a bicinchoninic acid (BCA) assay for protein quantitation, PICOGREEN™ (fluorescent nucleic acid stain of double stranded DNA) for DNA quantitation, and the like). In addition, the number of impurities is significantly reduced. For example, the protein impurities that are identifiable on a protein gel may be only a few different proteins (e.g., 2, 3, 5, 10, or 20), as opposed to hundreds, thousands, or tens of thousands of different proteins, as determined by methods such as silver staining of a protein SDS-PAGE gel. Impurities are virus preparation contaminants, such as DNA, RNA, protein, lipids, non-infectious particles and virus aggregates.

In one embodiment, the virus stock has a virus concentration of at least, or at least about, $10^5$ $TCID_{50}$/ml, $5\times10^5$ $TCID_{50}$/ml, $10^6$ $TCID_{50}$/ml, $5\times10^6$ $TCID_{50}$/ml, $10^7$ $TCID_{50}$/ml, $5\times10^7$ $TCID_{50}$/ml, $10^8$ $TCID_{50}$/ml, $5\times10^8$ $TCID_{50}$/ml, $10^9$ $TCID_{50}$/ml, $5\times10^9$ $TCID_{50}$/ml, $10^{10}$ $TCID_{50}$/ml, $5\times10^{10}$ $TCID_{50}$/ml, $10^{11}$ $TCID_{50}$/ml, $5\times10^{11}$ $TCID_{50}$/ml, or more, and a protein concentration of less than, or less than about, 100 ug/ml, 90 ug/ml, 80 ug/ml, 70 ug/ml, 60 ug/ml, 50 ug/ml, 40 ug/ml, 30 ug/ml, 20 ug/ml, 10 ug/ml or less, protein.

In one embodiment, the virus stock has a virus concentration of at least, or at least about, $10^5$ $TCID_{50}$/ml, $5\times10^5$ $TCID_{50}$/ml, $10^6$ $TCID_{50}$/ml, $5\times10^6$ $TCID_{50}$/ml, $10^7$ $TCID_{50}$/ml, $5\times10^7$ $TCID_{50}$/ml, $10^8$ $TCID_{50}$/ml, $5\times10^8$ $TCID_{50}$/ml, $10^9$ $TCID_{50}$/ml, $5\times10^9$ $TCID_{50}$/ml, $10^{10}$ $TCID_{50}$/ml, $5\times10^{10}$ $TCID_{50}$/ml, $10^{11}$ $TCID_{50}$/ml, $5\times10^{11}$ $TCID_{50}$/ml, or more, and a protein concentration of less than, or less than about, 100 fg/$TCID_{50}$, 90 fg/$TCID_{50}$, 80 fg/$TCID_{50}$, 70 fg/$TCID_{50}$, 60 fg/$TCID_{50}$, 50 fg/$TCID_{50}$, 40 fg/$TCID_{50}$, 30 fg/$TCID_{50}$, 20 fg/$TCID_{50}$, 15 fg/$TCID_{50}$, 10 fg/$TCID_{50}$, 5 fg/$TCID_{50}$, or less.

In one embodiment, the virus stock has a virus concentration of at least, or at least about, $10^5$ $TCID_{50}$/ml, $5\times10^5$ $TCID_{50}$/ml, $10^6$ $TCID_{50}$/ml, $5\times10^6$ $TCID_{50}$/ml, $10^7$ $TCID_{50}$/ml, $5\times10^7$ $TCID_{50}$/ml, $10^8$ $TCID_{50}$/ml, $5\times10^8$ $TCID_{50}$/ml, $10^9$ $TCID_{50}$/ml, $5\times10^9$ $TCID_{50}$/ml, $10^{10}$ $TCID_{50}$/ml, $5\times10^{10}$ $TCID_{50}$/ml, $10^{11}$ $TCID_{50}$/ml, $5\times10^{11}$ $TCID_{50}$/ml, or more, and a DNA concentration of less than, or less than about, 30 fg/$TCID_{50}$, 25 fg/$TCID_{50}$, 20 fg/$TCID_{50}$, 15 fg/$TCID_{50}$, 10 fg/$TCID_{50}$, 5 fg/$TCID_{50}$, 1 fg/$TCID_{50}$, 0.5 fg/$TCID_{50}$, or less.

In one embodiment, the virus stock has a virus concentration of at least, or at least about, $10^5$ $TCID_{50}$/ml, $5\times10^5$ $TCID_{50}$/ml, $10^6$ $TCID_{50}$/ml, $5\times10^6$ $TCID_{50}$/ml, $10^7$ $TCID_{50}$/ml, $5\times10^7$ $TCID_{50}$/ml, $10^8$ $TCID_{50}$/ml, $5\times10^8$ $TCID_{50}$/ml, $10^9$ $TCID_{50}$/ml, $5\times10^9$ $TCID_{50}$/ml, $10^{10}$ $TCID_{50}$/ml, $5\times10^{10}$ $TCID_{50}$/ml, $10^{11}$ $TCID_{50}$/ml, $5\times10^{11}$ $TCID_{50}$/ml, or more; a protein concentration of less than, or less than about, 100 $fg/TCID_{50}$, 90 $fg/TCID_{50}$, 80 $fg/TCID_{50}$, 70 $fg/TCID_{50}$, 60 $fg/TCID_{50}$, 50 $fg/TCID_{50}$, 40 $fg/TCID_{50}$, 30 $fg/TCID_{50}$, 20 $fg/TCID_{50}$, 15 $fg/TCID_{50}$, 10 $fg/TCID_{50}$, 5 $fg/TCID_{50}$, or less; and a DNA concentration of less than, or less than about, 30 $fg/TCID_{50}$, 25 $fg/TCID_{50}$, 20 $fg/TCID_{50}$, 15 $fg/TCID_{50}$, 10 $fg/TCID_{50}$, 5 $fg/TCID_{50}$, 1 $fg/TCID_{50}$, 0.5 $fg/TCID_{50}$, or less.

As will be appreciated by the skilled artisan, the methods described herein can be applied to purifying many viruses to a concentration of at least, or at least about $10^6$ $TCID_{50}$/ml, $10^7$ $TCID_{50}$/ml, $10^8$ $TCID_{50}$/ml, $10^9$ $TCID_{50}$/ml, $10^{10}$ $TCID_{50}$/ml, $10^{11}$ $TCID_{50}$/ml, $5\times10^{11}$ $TCID_{50}$/ml, or more. Thus, in one embodiment is a method of purifying a virus to a concentration of at least $10^6$ $TCID_{50}$/ml, comprising the sequential steps of obtaining a viral sample prepared under low protein conditions, concentrating the viral sample in a suitable buffer, and precipitating the virus in the viral sample, wherein the precipitated virus has a virus concentration of at least $10^7$ $TCID_{50}$/ml, thereby purifying a virus to a concentration of at least $10^7$ $TCID_{50}$/ml.

In one embodiment, the method purifies a virus to a concentration of at least, or at least about, $10^5$ $TCID_{50}$/ml, $5\times10^5$ $TCID_{50}$/ml, $10^6$ $TCID_{50}$/ml, $5\times10^6$ $TCID_{50}$/ml, $10^7$ $TCID_{50}$/ml, $5\times10^7$ $TCID_{50}$/ml, $10^8$ $TCID_{50}$/ml, $5\times10^8$ $TCID_{50}$/ml, $10^9$ $TCID_{50}$/ml, $5\times10^9$ $TCID_{50}$/ml, $10^{10}$ $TCID_{50}$/ml, $5\times10^{10}$ $TCID_{50}$/ml, $10^{11}$ $TCID_{50}$/ml, $5\times10^{11}$ $TCID_{50}$/ml, or more.

In another embodiment, the method purifies the virus to a concentration of at least, or at least about, $10^6$ $TCID_{50}$/ml, $5\times10^6$ $TCID_{50}$/ml, $10^7$ $TCID_{50}$/ml, $5\times10^7$ $TCID_{50}$/ml, $10^8$ $TCID_{50}$/ml, $5\times10^8$ $TCID_{50}$/ml, $10^9$ $TCID_{50}$/ml, $5\times10^9$ $TCID_{50}$/ml, $10^{10}$ $TCID_{50}$/ml, $5\times10^{10}$ $TCID_{50}$/ml, $10^{11}$ $TCID_{50}$/ml, $5\times10^{11}$ $TCID_{50}$/ml, or more, and a protein concentration of less than, or less than about, 100 ug/ml, 90 ug/ml, 80 ug/ml, 70 ug/ml, 60 ug/ml, 50 ug/ml, 40 ug/ml, 30 ug/ml, 20 ug/ml, or less, protein.

In one embodiment, the method purifies the virus to a concentration of at least, or at least about, $10^6$ $TCID_{50}$/ml, $5\times10^6$ $TCID_{50}$/ml, $10^7$ $TCID_{50}$/ml, $5\times10^7$ $TCID_{50}$/ml, $10^8$ $TCID_{50}$/ml, $5\times10^8$ $TCID_{50}$/ml, $10^9$ $TCID_{50}$/ml, $5\times10^9$ $TCID_{50}$/ml, $10^{10}$ $TCID_{50}$/ml, $5\times10^{10}$ $TCID_{50}$/ml, $10^{11}$ $TCID_{50}$/ml, $5\times10^{11}$ $TCID_{50}$/ml, or more, and a protein concentration of less than, or less than about, 100 $fg/TCID_{50}$, 90 $fg/TCID_{50}$, 80 $fg/TCID_{50}$, 70 $fg/TCID_{50}$, 60 $fg/TCID_{50}$, 50 $fg/TCID_{50}$, 40 $fg/TCID_{50}$, 30 $fg/TCID_{50}$, 20 $fg/TCID_{50}$, 15 $fg/TCID_{50}$, 10 $fg/TCID_{50}$, 5 $fg/TCID_{50}$, or less.

In one embodiment, the method purifies the virus to a concentration of at least, or at least about, $10^6$ $TCID_{50}$/ml, $5\times10^6$ $TCID_{50}$/ml, $10^7$ $TCID_{50}$/ml, $5\times10^7$ $TCID_{50}$/ml, $10^8$ $TCID_{50}$/ml, $5\times10^8$ $TCID_{50}$/ml, $10^9$ $TCID_{50}$/ml, $5\times10^9$ $TCID_{50}$/ml, $10^{10}$ $TCID_{50}$/ml, $5\times10^{10}$ $TCID_{50}$/ml, $10^{11}$ $TCID_{50}$/ml, $5\times10^{11}$ $TCID_{50}$/ml, or more, and a DNA concentration of less than, or less than about, 30 $fg/TCID_{50}$, 25 $fg/TCID_{50}$, 20 $fg/TCID_{50}$, 15 $fg/TCID_{50}$, 10 $fg/TCID_{50}$, 5 $fg/TCID_{50}$, 1 $fg/TCID_{50}$, 0.5 $fg/TCID_{50}$, or less.

In one embodiment, the method purifies the virus to a concentration of at least, or at least about, $10^6$ $TCID_{50}$/ml, $5\times10^6$ $TCID_{50}$/ml, $10^7$ $TCID_{50}$/ml, $5\times10^7$ $TCID_{50}$/ml, $10^8$ $TCID_{50}$/ml, $5\times10^8$ $TCID_{50}$/ml, $10^9$ $TCID_{50}$/ml, $5\times10^9$ $TCID_{50}$/ml, $10^{10}$ $TCID_{50}$/ml, $5\times10^{10}$ $TCID_{50}$/ml, $10^{11}$ $TCID_{50}$/ml, $5\times10^{11}$ $TCID_{50}$/ml, or more; a protein concentration of less than, or less than about, 100 $fg/TCID_{50}$, 90 $fg/TCID_{50}$, 80 $fg/TCID_{50}$, 70 $fg/TCID_{50}$, 60 $fg/TCID_{50}$, 50 $fg/TCID_{50}$, 40 $fg/TCID_{50}$, 30 $fg/TCID_{50}$, 20 $fg/TCID_{50}$, 15 $fg/TCID_{50}$, 10 $fg/TCID_{50}$, 5 $fg/TCID_{50}$, or less; and a DNA concentration of less than, or less than about, 30 $fg/TCID_{50}$, 25 $fg/TCID_{50}$, 20 $fg/TCID_{50}$, 15 $fg/TCID_{50}$, 10 $fg/TCID_{50}$, 5 $fg/TCID_{50}$, 1 $fg/TCID_{50}$, 0.5 $fg/TCID_{50}$, or less.

Another embodiment of the invention is a high purity virus or high purity virus stock produced by the methods described herein. In one embodiment is a composition comprising, consisting essentially of, or consisting of, a high purity virus or high purity virus stock produced by the methods described herein.

A further embodiment of the invention is a method of evaluating and/or validating a virus clearance process and the virus clearance unit operation used in the clearance process (e.g., a filter of flat membrane or hollow fiber type run in either direct flow or tangential flow modes; chromatographic steps including cationic exchange, anionic exchange, hydrophobic exchange, mixed-mode chromatography, affinity chromatography such as protein A or other ligand-based adsorption; virus inactivation process such as low pH, solvent/detergent, irradiation (gamma or ultraviolet), heat treatment).

As discussed above, one method for evaluating and/or validating a virus clearance process is a virus spiking study in a scaled-down model of the virus clearance process (also referred to herein as a "scaled virus clearance process"). The aim of the virus spiking study is to assess the effectiveness of a virus clearance unit in clearing viruses from the product (such as a biopharmaceutical) manufacturing processes. Higher virus titers allow larger virus reduction factors to be demonstrated and allow a more rigorous challenge to the virus clearance unit operation. However, in spiking studies, it is desirable to keep the volume of spiking material low, typically 10% or less, (vol/vol) relative to the sample to be tested so as not to unacceptably alter the sample product composition. As such, it is desirable to use a virus spike with high viral titer. Samples used in validating or evaluating a virus clearance process and/or a virus clearance unit used in a virus clearance process are any suitable samples of the manufacturing process feed. For example, a suitable sample is representative of a product produced during the manufacture of a biopharmaceutical. Examples include sample solutions comprising antibodies, recombinant proteins, vaccines, conjugated proteins, blood derivatives, plasma, and animal products, etc.

Thus, one embodiment is a method of evaluating and/or validating a virus clearance process, the method comprises spiking a sample with a high purity virus solution. In one embodiment, the high purity virus solution has a protein concentration of less than 100 $fg/TCID_{50}$, and a DNA concentration of less than 50 $fg/TCID_{50}$, to produce a test sample. In one embodiment, the high purity virus stock solution has a virus concentration of at least, or at least about, $10^6$ $TCID_{50}$/ml to at least, or at least about, $10^7$ $TCID_{50}$/ml, or more of high purity virus. A scaled virus clearance process, which is a scaled-down model of the virus clearance process, is tested using the test sample and analyzing the results of the virus clearance process, such that the amount of virus clearance evaluates and determines the validation of the virus clearance process.

In one embodiment, the high purity virus solution used in a method of evaluating and/or validating a virus clearance process comprises a protein concentration of less than, or less than about, 100 ug/ml, 90 ug/ml, 80 ug/ml, 70 ug/ml, 60 ug/ml, 50 ug/ml, 40 ug/ml, 30 ug/ml, 20 ug/ml, or less, protein. In another embodiment, the high purity virus solution used in a method of evaluating and/or validating a virus clearance process comprises a protein concentration of less than, or less than about, 100 fg/TCID$_{50}$, 90 fg/TCID$_{50}$, 80 fg/TCID$_{50}$, 70 fg/TCID$_{50}$, 60 fg/TCID$_{50}$, 50 fg/TCID$_{50}$, 40 fg/TCID$_{50}$, 30 fg/TCID$_{50}$, 20 fg/TCID$_{50}$, 15 fg/TCID$_{50}$, 10 fg/TCID$_{50}$, 5 fg/TCID$_{50}$, or less. In a further embodiment, the high purity virus solution used in a method of evaluating and/or validating a virus clearance process comprises a DNA concentration of less than, or less than about, 30 fg/TCID$_{50}$, 25 fg/TCID$_{50}$, 20 fg/TCID$_{50}$, 15 fg/TCID$_{50}$, 10 fg/TCID$_{50}$, 5 fg/TCID$_{50}$, 1 fg/TCID$_{50}$, 0.5 fg/TCID$_{50}$, or less. In a still further embodiment, the high purity virus solution used in a method of evaluating and/or validating a virus clearance process comprises at least, or at least about, $10^6$ TCID$_{50}$/ml, $5\times10^6$ TCID$_{50}$/ml, $10^7$ TCID$_{50}$/ml, $5\times10^7$ TCID$_{50}$/ml, $10^8$ TCID$_{50}$/ml, $5\times10^8$ TCID$_{50}$/ml, $10^9$ TCID$_{50}$/ml, $5\times10^9$ TCID$_{50}$/ml, $10^{10}$ TCID$_{50}$/ml, $5\times10^{10}$ TCID$_{50}$/ml, $10^{11}$ TCID$_{50}$/ml, $5\times10^{11}$ TCID$_{50}$/ml, or more virus.

In another embodiment, the high purity virus solution used in a method of evaluating and/or validating a virus clearance process comprises at least, or at least about, $10^5$ TCID$_{50}$/ml, $5\times10^5$ TCID$_{50}$/ml, $10^6$ TCID$_{50}$/ml, $5\times10^6$ TCID$_{50}$/ml, $10^7$ TCID$_{50}$/ml, $5\times10^7$ TCID$_{50}$/ml, $10^8$ TCID$_{50}$/ml, $5\times10^8$ TCID$_{50}$/ml, $10^9$ TCID$_{50}$/ml, $5\times10^9$ TCID$_{50}$/ml, $10^{10}$ TCID$_{50}$/ml, $5\times10^{10}$ TCID$_{50}$/ml, $10^{11}$ TCID$_{50}$/ml, $5\times10^{11}$ TCID$_{50}$/ml, or more virus, and a protein concentration of less than, or less than about, 100 ug/ml, 90 ug/ml, 80 ug/ml, 70 ug/ml, 60 ug/ml, 50 ug/ml, 40 ug/ml, 30 ug/ml, 20 ug/ml, or less, protein.

In one embodiment, the high purity virus solution used in a method of evaluating and/or validating a virus clearance process comprises at least, or at least about, $10^5$ TCID$_{50}$/ml, $5\times10^5$ TCID$_{50}$/ml, $10^6$ TCID$_{50}$/ml, $5\times10^6$ TCID$_{50}$/ml, $10^7$ TCID$_{50}$/ml, $5\times10^7$ TCID$_{50}$/ml, $10^8$ TCID$_{50}$/ml, $5\times10^8$ TCID$_{50}$/ml, $10^9$ TCID$_{50}$/ml, $5\times10^9$ TCID$_{50}$/ml, $10^{10}$ TCID$_{50}$/ml, $5\times10^{10}$ TCID$_{50}$/ml, $10^{11}$ TCID$_{50}$/ml, $5\times10^{11}$ TCID$_{50}$/ml, or more virus, and a protein concentration of less than, or less than about, 100 fg/TCID$_{50}$, 90 fg/TCID$_{50}$, 80 fg/TCID$_{50}$, 70 fg/TCID$_{50}$, 60 fg/TCID$_{50}$, 50 fg/TCID$_{50}$, 40 fg/TCID$_{50}$, 30 fg/TCID$_{50}$, 20 fg/TCID$_{50}$, 15 fg/TCID$_{50}$, 10 fg/TCID$_{50}$, 5 fg/TCID$_{50}$, or less.

In one embodiment, the high purity virus solution used in a method of evaluating and/or validating a virus clearance process comprises at least, or at least about, $10^5$ TCID$_{50}$/ml, $5\times10^5$ TCID$_{50}$/ml, $10^6$ TCID$_{50}$/ml, $5\times10^6$ TCID$_{50}$/ml, $10^7$ TCID$_{50}$/ml, $5\times10^7$ TCID$_{50}$/ml, $10^8$ TCID$_{50}$/ml, $5\times10^8$ TCID$_{50}$/ml, $10^9$ TCID$_{50}$/ml, $5\times10^9$ TCID$_{50}$/ml, $10^{10}$ TCID$_{50}$/ml, $5\times10^{10}$ TCID$_{50}$/ml, $10^{11}$ TCID$_{50}$/ml, $5\times10^{11}$ TCID$_{50}$/ml, or more virus, and a DNA concentration of less than, or less than about, 30 fg/TCID$_{50}$, 25 fg/TCID$_{50}$, 20 fg/TCID$_{50}$, 15 fg/TCID$_{50}$, 10 fg/TCID$_{50}$, 5 fg/TCID$_{50}$, 1 fg/TCID$_{50}$, 0.5 fg/TCID$_{50}$, or less.

In one embodiment, the high purity virus solution used in a method of evaluating and/or validating a virus clearance process comprises at least, or at least about, $10^5$ TCID$_{50}$/ml, $5\times10^5$ TCID$_{50}$/ml, $10^6$ TCID$_{50}$/ml, $5\times10^6$ TCID$_{50}$/ml, $10^7$ TCID$_{50}$/ml, $5\times10^7$ TCID$_{50}$/ml, $10^8$ TCID$_{50}$/ml, $5\times10^8$ TCID$_{50}$/ml, $10^9$ TCID$_{50}$/ml, $5\times10^9$ TCID$_{50}$/ml, $10^{10}$ TCID$_{50}$/ml, $5\times10^{10}$ TCID$_{50}$/ml, $10^{11}$ TCID$_{50}$/ml, $5\times10^{11}$ TCID$_{50}$/ml, or more virus; a protein concentration of less than, or less than about, 100 fg/TCID$_{50}$, 90 fg/TCID$_{50}$, 80 fg/TCID$_{50}$, 70 fg/TCID$_{50}$, 60 fg/TCID$_{50}$, 50 fg/TCID$_{50}$, 40 fg/TCID$_{50}$, 30 fg/TCID$_{50}$, 20 fg/TCID$_{50}$, 15 fg/TCID$_{50}$, 10 fg/TCID$_{50}$, 5 fg/TCID$_{50}$, or less; and a DNA concentration of less than, or less than about, 30 fg/TCID$_{50}$, 25 fg/TCID$_{50}$, 20 fg/TCID$_{50}$, 15 fg/TCID$_{50}$, 10 fg/TCID$_{50}$, 5 fg/TCID$_{50}$, or less.

In one embodiment of the method of evaluating and/or validating a virus clearance process, the test sample is spiked with at least, or at least about, 10%, 9%, 8%, 7%, 6%, 5%, 4%, 3%, 2%, 1%, 0.1%, 0.01%, 0.001%, 0.0001% (vol/vol) of any one of the high purity virus solutions above. In another embodiment of the method of evaluating and/or validating a virus clearance process, the test sample is spiked with at least, or at least about $10^5$ TCID$_{50}$/ml, $5\times10^5$ TCID$_{50}$/ml, $10^6$ TCID$_{50}$/ml, $5\times10^6$ TCID$_{50}$/ml, $10^7$ TCID$_{50}$/ml, $5\times10^7$ TCID$_{50}$/ml, $10^8$ TCID$_{50}$/ml, $5\times10^8$ TCID$_{50}$/ml, $10^9$ TCID$_{50}$/ml, $5\times10^9$ TCID$_{50}$/ml, $10^{10}$ TCID$_{50}$/ml, $5\times10^{10}$ TCID$_{50}$/ml, $10^{11}$ TCID$_{50}$/ml, $5\times10^{11}$ TCID$_{50}$/ml, or more virus from any one of the high purity virus solutions above.

If the virus is sufficiently removed from the test sample to meet regulatory standards, these data can be applied to virus clearance process validation. In one embodiment, the scaled virus clearance process comprises a filter.

A further embodiment is a method of evaluating and/or validating a virus clearance unit. The method comprises spiking a sample with a high purity virus solution as described above. In one embodiment, the high purity virus comprises a protein concentration of less than 100 fg/TCID$_{50}$, and a DNA concentration of less than 50 fg/TCID$_{50}$, to produce a test sample. In another embodiment, the high purity virus solution comprises at least, or at least about, $10^6$ TCID$_{50}$/ml of virus to at least, or at least about, $10^7$ TCID$_{50}$/ml of virus, or more. A virus clearance unit, which is a scaled-down model of the virus clearance unit used in a virus clearance process, is tested using the test sample and analyzing the results of the virus clearance unit, such that the amount of virus clearance determines the effectiveness of the virus clearance unit.

In one embodiment, the high purity virus solution used in a method of evaluating and/or validating a virus clearance unit comprises a protein concentration of less than, or less than about, 100 ug/ml, 90 ug/ml, 80 ug/ml, 70 ug/ml, 60 ug/ml, 50 ug/ml, 40 ug/ml, 30 ug/ml, 20 ug/ml, or less, protein. In another embodiment, the high purity virus solution used in a method of evaluating and/or validating a virus clearance unit comprises a protein concentration of less than, or less than about, 100 fg/TCID$_{50}$, 90 fg/TCID$_{50}$, 80 fg/TCID$_{50}$, 70 fg/TCID$_{50}$, 60 fg/TCID$_{50}$, 50 fg/TCID$_{50}$, 40 fg/TCID$_{50}$, 30 fg/TCID$_{50}$, 20 fg/TCID$_{50}$, 15 fg/TCID$_{50}$, 10 fg/TCID$_{50}$, 5 fg/TCID$_{50}$, or less. In a further embodiment, the high purity virus solution used in a method of evaluating and/or validating a virus clearance unit comprises a DNA concentration of less than, or less than about, 30 fg/TCID$_{50}$, 25 fg/TCID$_{50}$, 20 fg/TCID$_{50}$, 15 fg/TCID$_{50}$, 10 fg/TCID$_{50}$, 5 fg/TCID$_{50}$, 1 fg/TCID$_{50}$, 0.5 fg/TCID$_{50}$, or less. In a still further embodiment, the high purity virus solution used in a method of evaluating and/or validating a virus clearance unit comprises at least, or at least about, $10^6$ TCID$_{50}$/ml, $5\times10^6$ TCID$_{50}$/ml, $10^7$ TCID$_{50}$/ml, $5\times10^7$ TCID$_{50}$/ml, $10^8$ TCID$_{50}$/ml, $5\times10^8$ TCID$_{50}$/ml, $10^9$ TCID$_{50}$/ml, $5\times10^9$ TCID$_{50}$/ml, $10^{10}$ TCID$_{50}$/ml, $5\times10^{10}$ TCID$_{50}$/ml, $10^{11}$ TCID$_{50}$/ml, or more virus.

In another embodiment, the high purity virus solution used in a method of evaluating and/or validating a virus clearance unit comprises at least, or at least about, $10^5$ TCID$_{50}$/ml, $5\times10^5$ TCID$_{50}$/ml, $10^6$ TCID$_{50}$/ml, $5\times10^6$ TCID$_{50}$/ml, $10^7$ TCID$_{50}$/ml, $5\times10^7$ TCID$_{50}$/ml, $10^8$ TCID$_{50}$/ml, $5\times10^8$ TCID$_{50}$/ml, $10^9$ TCID$_{50}$/ml, $5\times10^9$ TCID$_{50}$/ml, $10^{10}$ TCID$_{50}$/ml, $5\times10^{10}$ TCID$_{50}$/ml, $10^{11}$ TCID$_{50}$/ml, $5\times10^{11}$ TCID$_{50}$/ml, or more virus, and a protein concentration of less than, or less than about, 100 ug/ml, 90 ug/ml, 80 ug/ml, 70 ug/ml, 60 ug/ml, 50 ug/ml, 40 ug/ml, 30 ug/ml, 20 ug/ml, or less, protein.

In one embodiment, the high purity virus solution used in a method of evaluating and/or validating a virus clearance unit comprises at least, or at least about, $10^5$ TCID$_{50}$/ml, $5\times10^5$ TCID$_{50}$/ml, $10^6$ TCID$_{50}$/ml, $5\times10^6$ TCID$_{50}$/ml, $10^7$ TCID$_{50}$/ml, $5\times10^7$ TCID$_{50}$/ml, $10^8$ TCID$_{50}$/ml, $5\times10^8$ TCID$_{50}$/ml, $10^9$ TCID$_{50}$/ml, $5\times10^9$ TCID$_{50}$/ml, $10^{10}$ TCID$_{50}$/ml, $5\times10^{10}$ TCID$_{50}$/ml, $10^{11}$ TCID$_{50}$/ml, $5\times10^{11}$ TCID$_{50}$/ml, or more virus, and a protein concentration of less than, or less than about, 100 fg/TCID$_{50}$, 90 fg/TCID$_{50}$, 80 fg/TCID$_{50}$, 70 fg/TCID$_{50}$, 60 fg/TCID$_{50}$, 50 fg/TCID$_{50}$, 40 fg/TCID$_{50}$, 30 fg/TCID$_{50}$, 20 fg/TCID$_{50}$, 15 fg/TCID$_{50}$, 10 fg/TCID$_{50}$, 5 fg/TCID$_{50}$, or less.

In one embodiment, the high purity virus solution used in a method of evaluating and/or validating a virus clearance unit comprises at least, or at least about, $10^5$ TCID$_{50}$/ml, $5\times10^5$ TCID$_{50}$/ml, $10^6$ TCID$_{50}$/ml, $5\times10^6$ TCID$_{50}$/ml, $10^7$ TCID$_{50}$/ml, $5\times10^7$ TCID$_{50}$/ml, $10^8$ TCID$_{50}$/ml, $5\times10^8$ TCID$_{50}$/ml, $10^9$ TCID$_{50}$/ml, $5\times10^9$ TCID$_{50}$/ml, $10^{10}$ TCID$_{50}$/ml, $5\times10^{10}$ TCID$_{50}$/ml, $10^{11}$ TCID$_{50}$/ml, $5\times10^{11}$ TCID$_{50}$/ml, or more virus, and a DNA concentration of less than, or less than about, 30 fg/TCID$_{50}$, 25 fg/TCID$_{50}$, 20 fg/TCID$_{50}$, 15 fg/TCID$_{50}$, 10 fg/TCID$_{50}$, 5 fg/TCID$_{50}$, 1 fg/TCID$_{50}$, 0.5 fg/TCID$_{50}$, or less.

In one embodiment, the high purity virus solution used in a method of evaluating and/or validating a virus clearance unit comprises at least, or at least about, $10^5$ TCID$_{50}$/ml, $5\times10^5$ TCID$_{50}$/ml, $10^6$ TCID$_{50}$/ml, $5\times10^6$ TCID$_{50}$/ml, $10^7$ TCID$_{50}$/ml, $5\times10^7$ TCID$_{50}$/ml, $10^8$ TCID$_{50}$/ml, $5\times10^8$ TCID$_{50}$/ml, $10^9$ TCID$_{50}$/ml, $5\times10^9$ TCID$_{50}$/ml, $10^{10}$ TCID$_{50}$/ml, $5\times10^{10}$ TCID$_{50}$/ml, $10^{11}$ TCID$_{50}$/ml, $5\times10^{11}$ TCID$_{50}$/ml, or more virus; a protein concentration of less than, or less than about, 100 fg/TCID$_{50}$, 90 fg/TCID$_{50}$, 80 fg/TCID$_{50}$, 70 fg/TCID$_{50}$, 60 fg/TCID$_{50}$, 50 fg/TCID$_{50}$, 40 fg/TCID$_{50}$, 30 fg/TCID$_{50}$, 20 fg/TCID$_{50}$, 15 fg/TCID$_{50}$, 10 fg/TCID$_{50}$, 5 fg/TCID$_{50}$, or less; and a DNA concentration of less than, or less than about, 30 fg/TCID$_{50}$, 25 fg/TCID$_{50}$, 20 fg/TCID$_{50}$, 15 fg/TCID$_{50}$, 10 fg/TCID$_{50}$, 5 fg/TCID$_{50}$, 1 fg/TCID$_{50}$, 0.5 fg/TCID$_{50}$, or less.

In one embodiment of the method of evaluating and/or validating a virus clearance unit, the test sample is spiked with at least, or at least about, 10%, 9%, 8%, 7%, 6%, 5%, 4%, 3%, 2%, or 1% (vol/vol) of any one of the high purity virus solutions above. In another embodiment of the method of evaluating and/or validating a virus clearance unit, the test sample is spiked with at least, or at least about $10^5$ TCID$_{50}$/ml, $5\times10^5$ TCID$_{50}$/ml, $10^6$ TCID$_{50}$/ml, $5\times10^6$ TCID$_{50}$/ml, $10^7$ TCID$_{50}$/ml, $5\times10^7$ TCID$_{50}$/ml, $10^8$ TCID$_{50}$/ml, $5\times10^8$ TCID$_{50}$/ml, $10^9$ TCID$_{50}$/ml, $5\times10^9$ TCID$_{50}$/ml, $10^{10}$ TCID$_{50}$/ml, $5\times10^{10}$ TCID$_{50}$/ml, $10^{11}$ TCID$_{50}$/ml, $5\times10^{11}$ TCID$_{50}$/ml, or more virus from any one of the high purity virus solutions above.

If the virus is sufficiently removed from the test sample to meet regulatory standards, the virus clearance unit is validated. In one embodiment, the virus clearance unit comprises a filter.

The virus removal achieved in a comprehensive scaled-down viral clearance study may be added to the viral clearance claims reported in drug application regulatory filing.

EXEMPLIFICATION

Example 1

Figure 2:
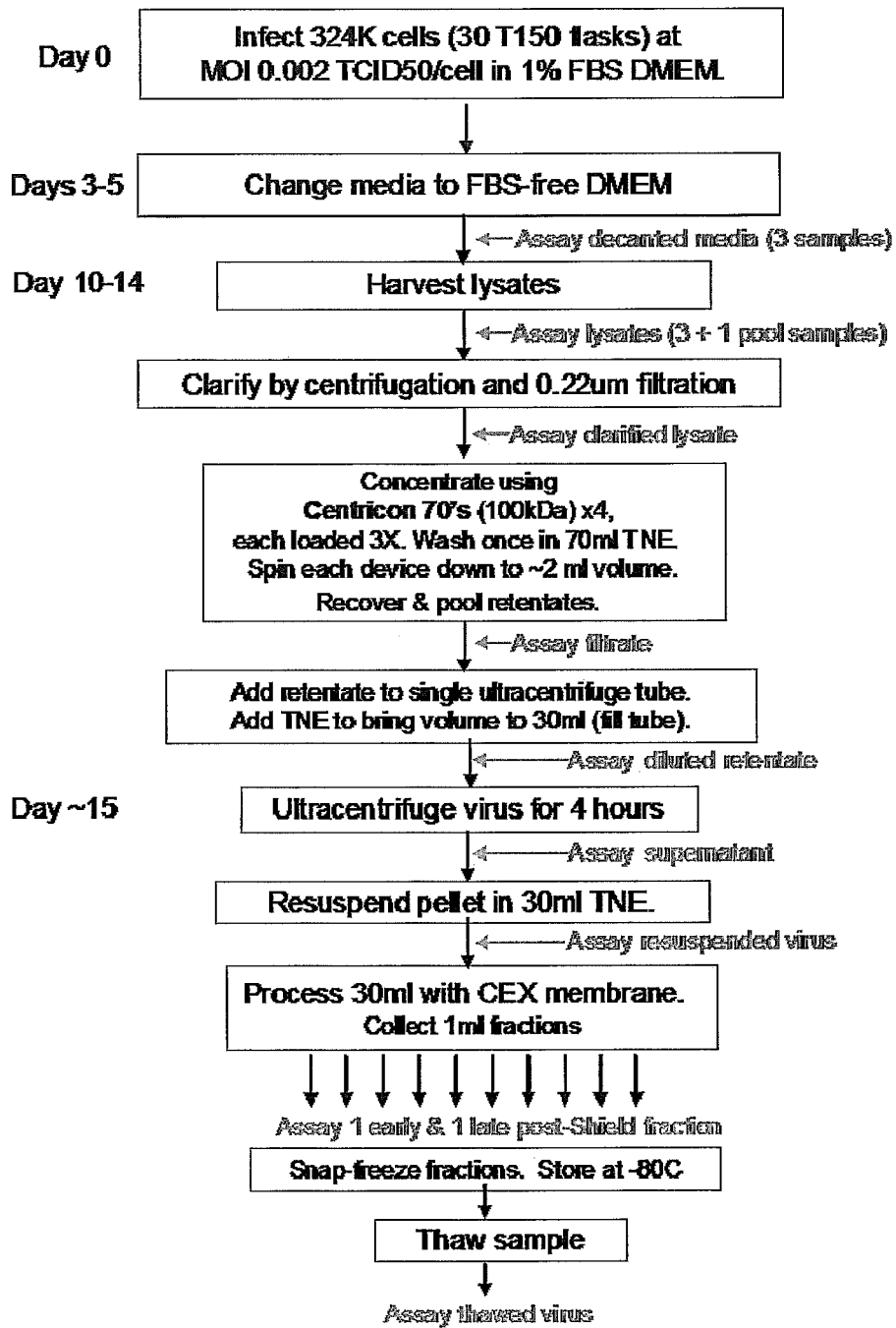
FIG. 2 is a flow chart demonstrating one embodiment of the invention.

MVM Propagation with 324K Cells (see FIGS. 2-4)

Materials:
Propagation cell line: 324K cells (Simian virus 40-transformed human fibroblasts), freshly thawed from stock.

Infection: Mouse minute virus (MVM) derived from an ATCC (catalog #VR-1346) virus stock was used to infect 324K host cells.

Media: DMEM with 10% fetal bovine serum "FBS", DMEM with 1% FBS, and DMEM without FBS. All supplemented with 0.1 mM non-essential amino acids, 2 mL L-glutamine, 0.2 units/ml penicillin/streptomycin. DMEM without FBS was supplemented with 0.1 mM non-essential amino acids, 2 mL L-glutamine, 0.1 units/ml penicillin/streptomycin.

Resuspension buffer: THE (10 mM Tris [pH 8.0], 150 mM NaCl, 1 mM EDTA).

Devices: Millipore cationic exchange (CEX) membrane adsorber comprising AMPS (2-Acrylamido-2-methyl-1-propanesulfonic acid) crosslinked by MBAm (N,N'-methylenebisacrylamide) on a polyethersulphone (PES) matrix, Millipore CENTRICON®-70 (a centrifugal filter unit) 100 kDa centrifugal ultrafiltration devices, and Millipore DURAPORE MILLEX™ (syringe filter unit with a PVDF membrane) 0.22 μm filters.

Methods:
Assays were carried out at multiple stages in the virus stock preparation methods described herein. In this example, assays were carried out at the points indicated in red in FIG. 2. The assay panel for each sample was as follows: virus titer (see below), BCA protein content (not on pre CENTRICON® (a centrifugal filter unit) samples), PICOGREEN™ (fluorescent nucleic acid stain of double stranded DNA) DNA content, and SDS-PAGE silver stain. A 1 ml sample was taken for assays at each sample point.

Virus titration: Unless noted otherwise, for each titration a 50 μl sample was made to a $10^{-2}$ dilution (i.e., diluted into 4.95 ml media). The exception was the CENTRICON® (a centrifugal filter unit) filtrate, which was assayed starting with undiluted sample. All samples were stored at 4° C. until titration, then at −80° C. after titration.

324K host cell line growth: Thirty T150 flasks of 324K cells were grown to confluency from a freshly thawed working stock vial. Media for growth: DMEM with 10% FBS.

Growth and infection schedule: Day 0: 324K infection—lift 324K cells using trypsin. Pool suspended cells and pellet at 1500 RPM for 10 min. Decant and discard media. Wash cells by resuspending in 50 ml complete DMEM with 1% FBS. Pellet cells as above. Decant and discard media. Pool resuspended cells into single sterile container and count the cells. Resulting cell count was 2.02E+06 cells/ml in a total of 60.0 ml. The total number of cells was 1.2E+08 cells. Therefore, the number of cells per confluent T150 was 9.2E+06 cells. A volume of 650 ml of cells at density of $2.0\times10^5$ cells/ml in DMEM with 1% FBS was prepared. Specifically, a 60 ml cells suspension was added to 590 ml DMEM with 1% FBS (total vol=650 ml). Counted cell density: 2.7E+05 cells/ml. MVM was added directly to suspended cells at MOI 0.002 TCID$_{50}$/cell. This requires adding 500 TCID$_{50}$ per ml of cells×650 ml=$3.3\times10^5$ total TCID50 added. MVM stock titer: $1\times10^8$ TCID$_{50}$/ml. $3.3\times10^5$ TCID50÷stock titer=0.0033 ml=3.3 μl of MVM stock added to 650 ml cells (may add 33 μl of a 1/10 dilution of stock). The cell suspension was thoroughly mixed. Transferred 20 ml of cell/virus suspension to each of 30 T150 flasks (label flasks 1-30). Target seeding=$4.0\times10^6$ cells/T150 flask. Actual seeding 5.4E6 cells/T150. Incubated cells at 37° C. 10% CO$_2$. At Days 3-4: Change to no serum media. Change media in ½ of the flasks on each day 3-4: On day 3, change the media in flasks 1-15; On day 4, change the media in flasks 15-30.

Media change procedure: Decant media in each flask into common pool. One pool will be made for each daily collection: Media d3 m/c (day 3 media change) from flasks 1-15; Media d4 m/c from flasks 15-30. Assay each decanted media pool. Wash each flask with 20 ml DMEM [no FBS]. Pour off and discard wash media. Replace media with 20 ml DMEM [no FBS] then continue cell incubation.

Day ~14: Harvest lysates. When cells show complete CPE (virus induced lysis), harvest the cell lysates by decanting the flasks into 3 pools. Lysate d3 m/c; Lysate d4 m/c. Assay each lysate pool (virus titer only). Combine lysates into a single pool. Assay combined lysate pool (virus titer only). Store lysate at 4° C. until processed by further steps.

Clarification: Centrifuge lysate by spinning at 2000×g for 15 minutes. Decant and save supernatants (discard pellets). Filter supernatant with 0.22 µm GP Express Plus (PVDF) Stericups. Total clarified lysate volume: 532.6 ml (determined by comparing weigh of empty and filled Stericups). Assay clarified lysate.

Concentration by CENTRICON® (a centrifugal filter unit): Prechill centrifuge to 4° C. Load 4 Plus CENTRICON® PLUS (a centrifugal filter unit) 100 kDa devices with 70 ml clarified lysate each=280 ml total. Spin CENTRICON® (a centrifugal filter unit) tubes until retentate volume=1-2 ml (Thermo Fisher tabletop centrifuge, rotor: 228, temp: 4° C., speed: 2390×g, total Spin Time (Spin 1): 13 min). Save the filtrate in common filtrate pool. Refill CENTRICON® (a centrifugal filter unit) tubes with 70 ml more lysate per device (pour on top of previous retentate). Spin CENTRICON® (a centrifugal filter unit) tubes again as above until retentate volume=1-2 ml. Total Spin Time (Spin 2): 16.45 min. Combine filtrate with previous filtrate from previous spin. Assay CENTRICON® (a centrifugal filter unit) filtrate (to detect any virus breakthrough and to visualize/quantitate proteins and DNA removed by CENTRICON® (a centrifugal filter unit) process). Set aside any remaining clarified lysate. Wash CENTRICON® (a centrifugal filter unit) tubes by filling with ~70 ml TNE. Spin CENTRICON® (a centrifugal filter unit) tubes again as above until retentate volume=1-2 ml. Total Spin Time (Spin 3—wash): 13 min). Discard wash filtrate. Invert device cores and collect retentates by centrifugation (Rotor: 228, Temp: 4° C., Speed: 1000×g, Time: 2 min). Combine retentates into common pool (brought up to 3 1 mL, so 1 mL sample can be taken).

Ultracentrifugation: Weigh a 30 ml ultracentrifuge tube with cap. Empty tube weight: 86.638 g. Bring retentate pool volume up to 31 ml using TNE (so that ultracentrifuge tube will be full when capped after removing 1 ml for assays). Assay diluted retentate. The expected virus concentration factor at this point is 18× from clarified lysate. Transfer diluted retentate pool to the 30 ml ultracentrifuge tube. Add TNE if needed to completely fill tube. Weigh filled, capped ultracentrifuge tube. Filled tube weight: 115.692 g. Total diluted retentate volume (filled—empty weight): 29.054 ml. Prechill ultracentrifuge to 4° C. Make a balance tube of same weight as virus tube. Ultracentrifuge virus (Ultracentrifuge rotor: SW28, Temp: 4° C., Speed: 25,000 RPM (112600×g), Time: 4 hr). Carefully decant supernatants from tube. Assay supernatant. Resuspend pellet in 15 ml TNE by pipetting up and down. Collect resuspended virus into new tube. Rinse ultracentrifuge tube with another 15 ml of TNE by pipetting up and down. Combine rinse with first pellet resuspension to form a 30 ml pool of virus. Assay resuspended pellet pool.

Sterile Filtration: Sterile filter using 0.22 µm DURAPORE MILLEX™ (syringe filter unit with a PVDF membrane) syringe filter. Assay post-0.22 µm filtrates.

CEX membrane adsorber processing: Pass 30 ml virus pool through CEX membrane absorber device. CEX procedure: Pre-wet CEX device at 30 psi for 10 minutes with MilliQ. Repeat device pre-wet with buffer. After pre-wet, remove device from pressure source and attach hydrophobic MILLEX™ (syringe filter unit with a hydrophobic membrane and 0.22 micron pore size) to V SHIELD™ (side vent for the membrane adsorber unit) vent. Using a sterile syringe, slowly expel remaining volume in the CEX device. Be careful not to apply full pressure to device, some liquid should remain between membrane layers. Using a syringe pump, set syringe diameter and flow rate (2 mL/min). Load syringe with virus prep and remove all air from syringe. Attach pre-wetted CEX to syringe and secure in syringe pump holder. Using tubing attached to the outlet side of the CEX device, start syringe pump and collect filtrate in sterile container. After all material has been pushed through CEX, stop pump, remove syringe and allow volume in tubing to drain into collection vessel. Collect CEX filtrate as 1 ml aliquots, numbered 1-14 in 2 ml cyrovials. Assay CEX-processed virus fractions 2 (early fraction) and 14 (late fraction).

Virus storage: Snap-freeze vials by dipping in isopropanol/dry ice bath. Immediately transfer samples to storage at −80° C.

Thaw virus samples and check for aggregation by filter sizing: Thaw an aliquot of virus in 37° C. water bath. Assay thawed virus. Pass each thawed aliquot through a 0.1 µm syringe filter. Assay 0.1 µm filtered viruses.

TABLE 1

Results (VSP-PROC-004- Evaluation run #1)

| Tab | Sample Name | Titer (log TCID50) |
| --- | --- | --- |
| 1 | Day 3 Media decanted at change to no FBS | 6.25 |
| 2 | Day 4 Media decanted at change to no FBS | 6.56 |
| 3 | Lysate d3 | 7.75 |
| 4 | Lysate d4 | 7.75 |
| 5 | Lysate pool | 7.50 |
| 6 | Clarified lysate | 7.81 |
| 7 | CENTRICON ® (a centrifugal filter unit) filtrate pool | 4.69 |
| 8 | Diluted Retentate | 8.75 |
| 9 | Ultracentrifuge Supernatant | 7.63 |
| 10 | Resuspended pellet | 9.00 |
| 11 | 0.22 um filtered virus | 8.88 |
| 12 | CEX-processed virus fraction 2 | 8.56 |
| 13 | CEX-processed virus fraction 14 | 8.56 |
| 14 | Thawed 0.22 um filtered virus (sample 11) | 8.81 |
| 15 | Thawed CEX processed virus (sample 13) | 8.81 |
| 16 | Thawed 0.1 um filtered virus | 8.88 |
| 17 | Thawed 0.1 um filtered CEX-processed virus (sample 13) | 8.81 |

TABLE 2

Summary of Results

| Sample Name | Checkpoint #2 | | Checkpoint #3 | |
| --- | --- | --- | --- | --- |
| | log $TCID_{50}$/ml | Total virus | log $TCID_{50}$/ml | Total Virus |
| Harvested lysate | 7.81 | 10.59 | 7.88 | 10.65 |
| CENTRICON ® (a centrifugal filter unit) processed | 9.00 | 10.48 | 8.81 | 10.29 |
| Ultracentrifuged | 9.00 | 10.48 | 8.81 | 10.29 |
| CEX processed | 8.81 | 10.29 | 8.56 | 10.04 |

Conclusions 324K cells produced ~7.7 log $TCID_{50}$/ml in the raw lysate. Removal of serum did not decrease titers from those previously seen in FBS-containing preps. CENTRICON® (a centrifugal filter unit) allowed for recovery of most of the virus, but did not remove contaminating proteins. Centrifugation recovered most of the remaining virus, with a considerable increase in purity. Passage of resuspended pellet across Millipore CEX membrane adsorber removed most of the remaining contaminants. Consistent results found for evaluation runs 1-4, which were all performed using this method.

Example 2

Figure 7:
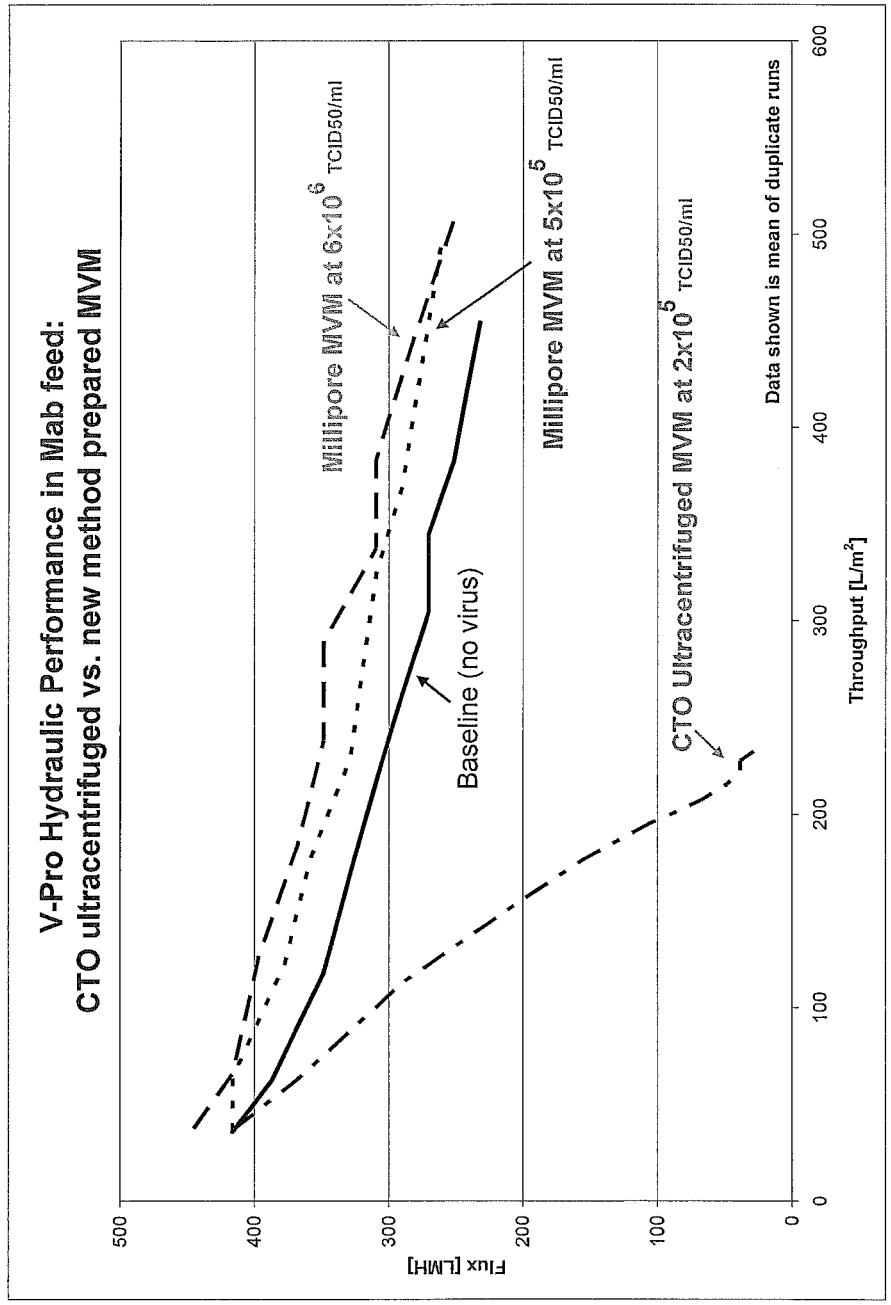
FIG. 7 is a graph demonstrating hydraulic performance of a test filter (VIRESOLVE® PRO (V-PRO)) (parvovirus-retentive filter) using a sample spiked with a virus prepared as described herein and compared with a sample spiked with a standard virus preparation typically used for validation studies, which was provided by a contract testing organization (CTO). The virus preparation by the CTO used an ultracentrifugation method. MVM prepared as described herein was spiked into a monoclonal antibody feed (9.1 g/L) that had previously presented filtration challenges due to interactions with virus spikes. MVM produced by the CTO spiked to a concentration of $2\times10^5$ $TCID_{50}$/ml resulted in a dramatic decrease in throughput across the filter V-Pro, compared to the unspiked feed baseline (no virus). In contrast, the MVM prepared as described herein, had no impact on hydraulic performance at a spike level of $5\times10^5$ $TCID_{50}$/ml, nor did a ten-fold greater spike to $6\times10^6$ $TCID_{50}$/ml.

MVM Propagation with A9 Cells (see FIGS. 5-7)

The method of Example 1 was repeated with the substitution of A9 cells (ATCC) for the 324K host cells and Advanced™ DMEM (Invitrogen product #12491-015) for DMEM. Post CEX-fractions were collected in 1 ml rather than 2 ml fractions. The protocol was otherwise identical. The results are shown in FIG. 5A, FIG. 5B and FIG. 6.

Results

Observation of cell progress post-infection: Day 2: 100% confluent; Day 4: 90% confluent—10% detached; Day 7: 60% lysis; Day 8: 60-70% lysis; Day 9: Same as day 8; harvest on day 10.

TABLE 3

Results (VSP-PROC-010-A9)

| Tab | Sample Name | Titer (log $TCID_{50}$) |
|---|---|---|
| 1 | Day 3 decanted media | 6.69 |
| 2 | Cl. lysate Day 10 | 9.75 |
| 3 | Cl. lysate Day 11 | 9.75 |
| 4 | Pooled clarified lysate | 9.88 |
| 5 | CENTRICON ® (a centrifugal filter unit) filtrate | 6.69 |
| 6 | Diluted Retentate | 10.31 |
| 7 | U/C supernatant | 9.19 |
| 8 | U/C pellet | 10.56 |
| 9 | Fraction 7 | 10.50 |
| 10 | Fraction 20 | 10.31 |

TABLE 4

Summary of Results

| Sample name | A9 evaluation log $TCID_{50}$/ml | Total virus |
|---|---|---|
| Harvested lysate | 9.88 | 12.66 |
| CENTRICON ® (a centrifugal filter unit) processed | 10.31 | 11.79 |
| Ultra centrifuged | 10.56 | 12.04 |
| CEX Processed | 10.41 | 11.88 |

Conclusions

A9 cells produced 9.75 log $TCID_{50}$/ml in the raw cell lysate. Increased titer in the harvest led to a final virus stock with a concentration of 10.5 log $TCID_{50}$/ml. SDS-PAGE showed that the virus harvests from the A9 propagation had more protein than the 324K lysates. However, despite the appearance of more protein in the final virus stock (these may be viral proteins), the final purity as measured by protein/infectious virus was ~2-5 fg protein/$TCID_{50}$. Given that the media is still serum-free and the cell protein background would be expected to be equivalent, these may be viral proteins (and thus a consequence of the greater virus titer).

Example 3

Figure 8:
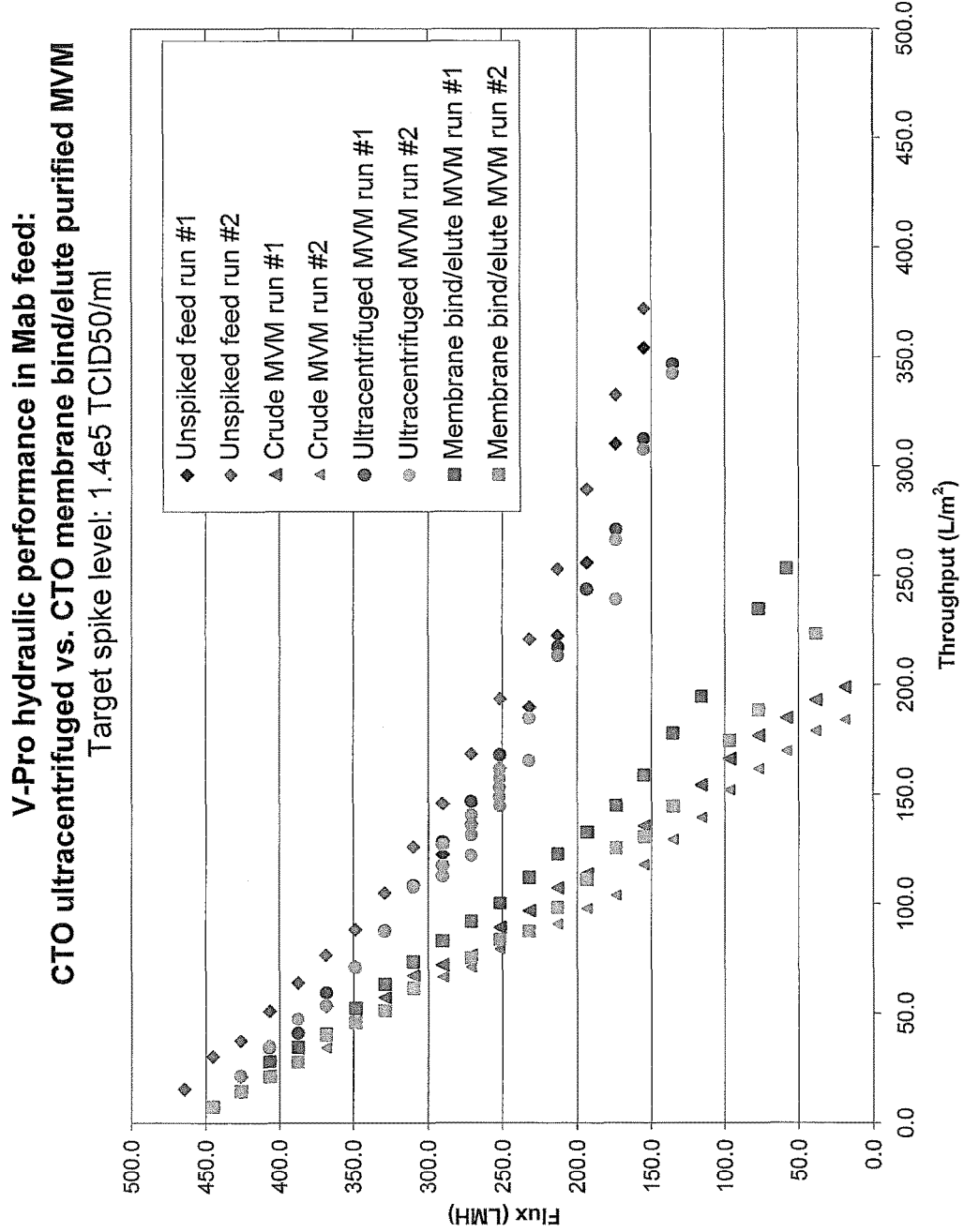
FIG. 8 is a graph of three CTO MVM spiking stocks prepared by different methods evaluated for their hydraulic performance when spiked into a monoclonal antibody (Mab) feed and processed across (VIRESOLVE® PRO (V-PRO)) (parvovirus-retentive filter).
Figure 9:
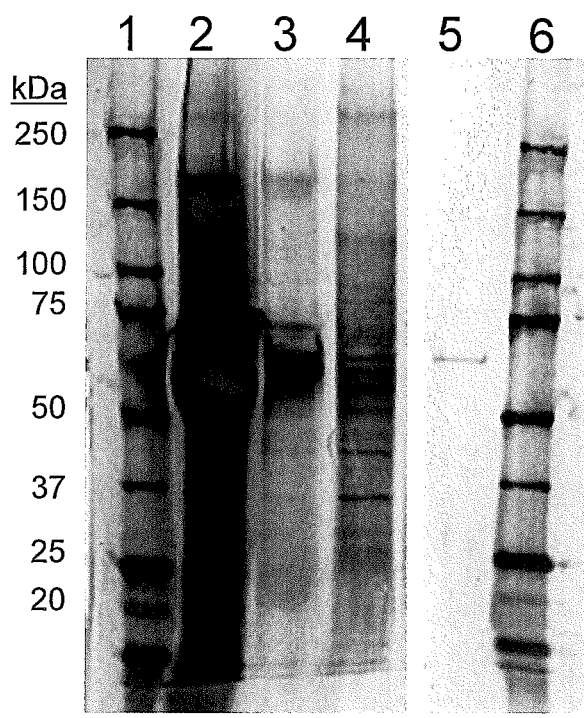
FIG. 9 is a photograph of an SDS-PAGE gel analysis of three standard CTO MVM preparations and an MVM preparation by the method of the present invention. Proteins in 4-15% gradient gel were visualized by silver stain. Each sample lane was loaded with 10 μl of sample. Lane 1: Molecular weight markers; Lane 2: CTO crude MVM preparation ($2.3\times10^7$ $TCID_{50}$/ml); Lane 3: CTO ultracentrifuge purified MVM preparation ($1.8\times10^7$ $TCID_{50}$/ml); Lane 4 ($2.3\times10^7$ $TCID_{50}$/ml): CTO Q-membrane bind/elute purified MVM preparation; Lane 5: MVM preparation of the present invention ($6.5\times10^8$ $TCID_{50}$/ml); Lane 6: Molecular weight markers.

Evaluation of Different Standard CTO Spiking Stock Solutions on Hydraulic Performance (see FIGS. 8-9)

Three CTO MVM spiking stocks prepared by different methods were evaluated for their hydraulic performance when spiked into a monoclonal antibody (Mab) feed and processed across (VIRESOLVE® PRO (V-PRO)) (parvovirus-retentive filter). The crude preparation was only clarified to remove cell debris and subjected to no further purification. The ultracentrifuged preparation was purified by pelleting the virus in infected cell culture lysate by ultracentrifugation, discarding the supernatant, and then resuspending the virus in PBS. The membrane bind/elute purified preparation was made by passing clarified, infected cell culture lysate across a membrane adsorber with positively charged Q chemistry. The virus bound to the membrane, and was then eluted with a phosphate buffer containing 400 mM NaCl. MVM preparations made by the ultracentrifugation and membrane bind/elute purified methods are sold by the CTO to customers for use in their spiking studies.

The targeted spike level for all three stocks was $1.4 \times 10^5$ $TCID_{50}$/ml. Each condition was run in duplicate (run #1 and run #2). The actual titers achieved in the feed post-spike were crude: $2 \times 10^5$ $TCID_{50}$/ml; ultracentrifuged: $4 \times 10^4$ $TCID_{50}$/ml; and membrane bind/elute purified: $6 \times 10^4$ $TCID_{50}$/ml. Notably, the hydraulic performance of the membrane bind/elute purified preparation was no better than that of unpurified crude virus. In this comparison, the ultracentrifuged preparation had the best performance of the three CTO preparations, with throughput similar to that of unspiked feed (at the spike level of $4 \times 10^4$ $TCID_{50}$/ml). However, as described in the above examples, the virus preparations of the present invention performed significantly better than the CTO virus preparations (see, e.g., FIG. 7).

TABLE 5

Summary of the biomolecular characterization of standard CTO MVM virus stock preparations (ultracentrifuge preparation and Q-membrane preparation) vs. MVM virus stock preparation by the method of the present invention.

| Source | Virus | Preparation type | Stock titer (log $TCID_{50}$/ml) | Protein (ug/ml) | DNA (ug/ml) | Protein/virus (fg/$TCID_{50}$) | DNA/virus (fg/$TCID_{50}$) |
|---|---|---|---|---|---|---|---|
| CTO | MVM | crude | 7.4 | *n.d. | 5.5 | *n.d. | 240 |
| CTO | MVM | ultracentrifuged | 7.3 | 159.0 | 1.9 | 8738 | 107 |
| CTO | MVM | Q-membrane | 7.4 | 266.0 | 4.4 | 11611 | 190 |

TABLE 5-continued

Summary of the biomolecular characterization of standard CTO MVM virus stock preparations (ultracentrifuge preparation and Q-membrane preparation) vs. MVM virus stock preparation by the method of the present invention.

| Source | Virus | Preparation type | Stock titer (log $TCID_{50}$/ml) | Protein (ug/ml) | DNA (ug/ml) | Protein/virus (fg/$TCID_{50}$) | DNA/virus (fg/$TCID_{50}$) |
|---|---|---|---|---|---|---|---|
| Millipore | MVM | method of the present invention | 8.8 | 11.0 | 1.9 | 17 | 3 |

Protein was quantified by Micro BCA assay. *n.d. Not determined. Media components present in the crude virus stock interfere with the Micro BCA protein assay. DNA was quantified by PICOGREEN™ (fluorescent nucleic acid stain of double stranded DNA) assay. As can be seen in Table 5, the CTO virus preparations have significantly more protein and DNA content.

The amount of protein/virus has been found to correlate directly with the potential of a virus preparation to cause filter fouling. In addition to the assays performed above, the three standard CTO MVM preparations and an MVM preparation by the method of the present invention were analyzed by SDS-PAGE gel and silver stain analysis. FIG. 9 is a photograph of a silver stained 4-15% gradient SDS-PAGE gel. Each sample lane was loaded with 10 µl of sample. Lane 1: Molecular weight markers; Lane 2: CTO crude MVM preparation ($2.3 \times 10^7$ $TCID_{50}$/ml); Lane 3: CTO ultracentrifuge-purified MVM preparation ($1.8 \times 10^7$ $TCID_{50}$/ml); Lane 4: CTO Q-membrane bind/elute-purified MVM preparation ($2.3 \times 10^7$ $TCID_{50}$/ml); Lane 5: MVM preparation using the methods of the present invention ($6.5 \times 10^8$ $TCID_{50}$/ml); Lane 6: Molecular weight markers.

As demonstrated in FIG. 9, each of the CTO virus preparations have considerable total numbers of proteins present (see number of bands of proteins and smear of proteins in each lane), as well as total amount of protein per sample (demonstrated as total staining amount). In comparison, the method of the present invention produces a virus preparation with minimal protein content, both quantitatively and qualitatively, as described herein.

Example 4

Comparison of Various Cationic Exchange Media Used for Flow-Through MVM Virus Stock Purification An MVM virus stock (previously purified by buffer exchange into TNE and ultracentrifugation) was passed through various cationic exchange media. The flow-through material was then assayed for virus titer and protein content by MicroBCA assay following the manufacturer's protocol. The devices listed in Table 6 all removed significant amount of protein impurities while maintaining the titer of the virus preparation. Millipore CEX (membrane adsorber comprising AMPS (2-Acrylamido-2-methyl-1-propanesulfonic acid) crosslinked by MBAm (N,N'-methylenebisacrylamide) on a poly ether sulphone (PES) matrix) and Sartobind S15 (Sartorius) are both cation exchange membrane adsorbers. Pro Res-S (Millipore) is a monodispersed polymethacrylate strong cation exchange resin.

TABLE 6

Comparison of various cationic exchange media used for flow-through MVM virus stock purification.

| Virus treatment | Virus titer (log TCID50/ml) | Protein content (ug/ml) | Protein reduction |
|---|---|---|---|
| Untreated MVM stock | 8.7 | 15.6 | |
| Millipre CEX | 8.4 | 3.2 | 79% |
| Sartobind S15 | 8.7 | 5.6 | 64% |
| Pro Res-S | 8.7 | 4.5 | 71% |

As demonstrated in Table 6, a variety of cationic exchange media in a flow-through mode can be used to produce high purity virus solutions using the methods as described herein.

Example 5

MVM Stocks in a Variety of Buffers Treated Using a Cationic Exchange (CEX) Membrane Adsorber MVM stocks in a variety of buffers were treated using a cationic exchange (CEX) membrane adsorber comprising AMPS (2-Acrylamido-2-methyl-1-propanesulfonic acid) cross-linked by MBAm (N,N'-methylenebisacrylamide) on a poly ether sulphone (PES) matrix in a flow-through mode. As demonstrated in Table 7, removal of protein impurities was achieved in each of these conditions without significant loss of viral titer.

TABLE 7

MVM stocks in a variety of buffers treated using a cationic exchange (CEX) membrane adsorber.

| MVM buffer | Pretreatment virus titer (log $TCID_{50}$/ml) | Pretreatment protein content (ug/ml) | Post-treatment virus titer (log $TCID_{50}$/ml) | Post-treatment protein content (ug/ml) | Protein reduction |
|---|---|---|---|---|---|
| TNE | 8.50 | 68 | 8.31 | 55 | 19% |
| PBS | 8.38 | 64 | 7.94 | 44 | 31% |
| TE | 8.50 | 51 | 8.75 | 27 | 47% |

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A method of preparing a high purity virus stock solution, wherein the virus stock solution comprises a protein concentration of less than 100 fg/TCID$_{50}$ suitable for validation of retentive filters, the method comprising the sequential steps of:
   (a) harvesting the culture supernatant of virus-infected cells grown under low serum conditions, wherein the culture supernatant is harvested after virus-induced cell lysis, thereby obtaining a viral sample;
   (b) concentrating the viral sample by ultrafiltration, tangential flow filtration, dialysis, or a combination of the foregoing, and exchanging the culture supernatant for a suitable buffer; and
   (c) precipitating the virus in the viral sample by ultracentrifugation, chemical-induced precipitation, chromatographic binding, polymer-induced aggregation, or a combination thereof, wherein the precipitated virus comprises a protein concentration of less than 100 fg/TCID$_{50}$;
   thereby preparing a high purity virus stock solution suitable for validation of retentive filters.

2. The method of claim 1, further comprising subjecting the precipitated virus to chromatographic polishing to remove trace impurities.

3. The method of claim 1, wherein the virus stock solution has a protein concentration of less than about 20 fg/TCID$_{50}$.

4. The method of claim 1, wherein the virus is a parvovirus or a xenotropic murine leukemia virus (X-MuLV).

5. A method of purifying a virus to a concentration of at least 10$^6$ TCID$_{50}$/ml and a protein concentration of less than 100 fg/TCID$_{50}$ suitable for validation of retentive filters, the method comprising the sequential steps of:
   (a) harvesting the culture supernatant of virus-infected cells grown under serum-free conditions, wherein the culture supernatant is harvested after virus-induced cell lysis, thereby obtaining a viral sample;
   (b) concentrating the viral sample by ultrafiltration, tangential flow filtration, dialysis, or a combination of the foregoing, and exchanging the culture supernatant for a suitable buffer;
   (c) precipitating the virus in the viral sample by ultracentrifugation, chemical-induced precipitation, chromatographic binding, polymer-induced aggregation, or a combination thereof, wherein the precipitated virus has a virus concentration of at least 10$^6$ TCID$_{50}$/ml and a protein concentration of less than 100 fg/TCID$_{50}$; and
   (d) subjecting the precipitated virus to chromatographic polishing to remove trace impurities,
   thereby purifying a virus to a concentration of at least 10$^6$ TCID$_{50}$/ml and a protein concentration of less than 100 fg/TCID$_{50}$ suitable for validation of retentive filters.

6. The method of claim 5, wherein the virus stock solution has a protein concentration of less than about 60 fg/TCID$_{50}$.

7. The method of claim 5, wherein the virus is a parvovirus or a xenotropic murine leukemia virus (X-MuLV).

8. A method of evaluating a virus clearance process, the method comprising:
   (a) spiking a sample with a virus solution produced by the method of claim 1, thereby producing a test sample;
   (b) testing a scaled virus clearance process using the test sample; and
   (c) analyzing the results of the virus clearance process, wherein the amount of virus clearance determines the virus removal capability of the virus clearance process, thereby evaluating the virus clearance process.

9. The method of claim 8, wherein the virus clearance process comprises virus removal, virus inactivation, or a combination thereof.

10. The method of claim 8, wherein the virus is a parvovirus or a xenotropic murine leukemia virus (X-MuLV).

11. A method of evaluating a virus clearance process, the method comprising:
    (a) spiking a sample with a virus solution, wherein the virus solution is prepared by the method of claim 6, thereby producing a test sample;
    (b) testing a scaled virus clearance process using the test sample; and
    (c) analyzing the results of the virus clearance process, wherein the amount of virus clearance determines the virus removal capability of the virus clearance process, thereby evaluating the virus clearance process.

12. The method of claim 11, wherein the chromatographic polishing comprises cation exchange flow-through chromatography on a membrane or bead-based matrix.

13. The method of claim 2, wherein the further processing to remove trace impurities comprises flow-through chromatography.

14. The method of claim 13, wherein the flow-through chromatography comprises cation exchange flow-through chromatography on a membrane or bead-based matrix.

15. The method of claim 7, wherein the virus is a parvovirus.

16. The method of claim 15, wherein the parvovirus is minute virus of mice (MVM).

17. The method of claim 14, wherein the virus is a parvovirus.

18. The method of claim 17, wherein the parvovirus is minute virus of mice (MVM).

19. The method of claim 14, wherein the chromatography comprises AMPS (2-Acrylamido-2-methyl-1-propanesulfonic acid) cross-linked by MBAm (N,N'-methylenebisacrylamide) on a poly ether sulphone (PES) matrix.

* * * * *